United States Patent
Sanfilippo et al.

(10) Patent No.: US 10,071,975 B2
(45) Date of Patent: Sep. 11, 2018

(54) MACROCYCLIC AMIDINOUREA DERIVATIVES, METHODS OF PREPARATION AND USES THEREOF AS CHITINASE INHIBITORS

(71) Applicant: CYGNET BIOSCIENCES B.V., Willemstad (CW)

(72) Inventors: Stefania Sanfilippo, Siena (IT); Brunella Posteraro, Rome (IT); Maurizio Sanguinetti, Rome (IT); Maurizio Botta, Siena (IT); Giorgio Maccari, Siena (IT); Filomena De Luca, Siena (IT); Jean-Denis Docquier, Siena (IT); Davide Deodato, Siena (IT)

(73) Assignee: CYGNET BIOSCIENCES B.V., Willemstad (CW)

( * ) Notice: Subject to any disclaimer, the term of this patent is extended or adjusted under 35 U.S.C. 154(b) by 0 days.

(21) Appl. No.: 14/899,872

(22) PCT Filed: Jun. 18, 2014

(86) PCT No.: PCT/EP2014/062896
§ 371 (c)(1),
(2) Date: Dec. 18, 2015

(87) PCT Pub. No.: WO2014/202697
PCT Pub. Date: Dec. 24, 2014

(65) Prior Publication Data
US 2016/0137617 A1    May 19, 2016

Related U.S. Application Data

(60) Provisional application No. 61/836,401, filed on Jun. 18, 2013.

(51) Int. Cl.
| | | |
|---|---|---|
| *C07D 273/00* | (2006.01) | |
| *C07D 413/04* | (2006.01) | |
| *C07C 279/24* | (2006.01) | |
| *A61K 31/395* | (2006.01) | |
| *A61K 31/4192* | (2006.01) | |
| *A61K 45/06* | (2006.01) | |
| *C07C 271/20* | (2006.01) | |

(52) U.S. Cl.
CPC .......... *C07D 273/00* (2013.01); *A61K 31/395* (2013.01); *A61K 31/4192* (2013.01); *A61K 45/06* (2013.01); *C07C 271/20* (2013.01); *C07C 279/24* (2013.01); *C07D 413/04* (2013.01)

(58) Field of Classification Search
CPC ............................. C07D 273/00; C07D 413/04
See application file for complete search history.

(56) References Cited

U.S. PATENT DOCUMENTS 8,685,953 B2    4/2014  Botta et al.

FOREIGN PATENT DOCUMENTS

WO    2009113033 A2    9/2009

OTHER PUBLICATIONS

Slverman. The Organic Chemistry of Drug Design and Action, 2004, 25-34.*
List of Azole Antifungals—Drugs.com, https://www.drugs.com/drugclass/azoleantifungals.html, accessed Jun. 14, 2017, attached as PDF.*
Sheehan. Clinical Microbiology Reviews, 1999, 12(1), 40-79.*
Manetti et al., "Synthesis of New Linear Guanidines and Macrocyclic Amidinourea Derivatives Endowed with High Antifungal Activity against *Candida* spp. and *Aspergillus* spp.", Journal of Medicinal Chemistry Letter, 2009, vol. 52, No. 23, pp. 7376-7379.
Sanguinetti et al., "Novel Macrocyclic Amidinoureas: Potent Non-Azole Antifungals Active against Wild-Type and Resistant *Candida* Species", ACS Medicinal Chemistry Letters, 2013, vol. 4, No. 9, pp. 852-857.
International Search Report and Written Opinion for International Application No. PCT/EP2014/062896. (dated Sep. 3, 2014)(13 pages).
"The Organic Chemistry of Drug Design and Drug Action, Third Edition" Richard B. Silverman & Mark W. Holladay, 2014, pp. xv-xvi ("Preface to the Second Edition").

* cited by examiner

*Primary Examiner* — Noble E Jarrell
(74) *Attorney, Agent, or Firm* — Lucas & Mercanti, LLP

(57) ABSTRACT

The present invention relates to macrocyclic amidinourea derivatives of formula 8, methods of preparation and uses thereof, pharmaceutical compositions in particular to be used as chitinase inhibitors in the treatment of a fungal infection.

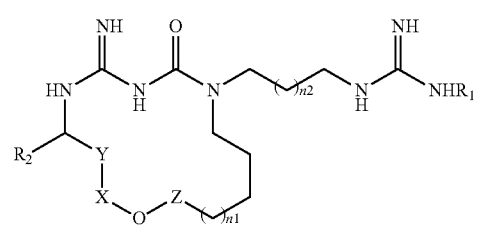

21 Claims, No Drawings

MACROCYCLIC AMIDINOUREA DERIVATIVES, METHODS OF PREPARATION AND USES THEREOF AS CHITINASE INHIBITORS

CROSS-REFERENCE TO RELATED APPLICATIONS

This application is a 371 of PCT/EP2014/062896, filed Jun. 18, 2014, which claims the benefit of U.S. provisional patent application Ser. No. 61/836,401, filed Jun. 18, 2013.

FIELD OF THE INVENTION

The present invention relates to macrocyclic amidinourea derivatives, methods of preparation and uses thereof, pharmaceutical compositions in particular to be used as chitinase inhibitors.

BACKGROUND OF THE INVENTION

The epidemiology of fungal infections is an evolving issue since the late 1960s when, as a consequence of the development of antibiotic therapies, a drastic rise of mycoses was observed. Today, fungal infections represent a major global health threat and the increasing incidence of invasive and opportunistic mycoses is often associated with excessive morbidity and mortality. Fungal infections have increased in incidence during last decades often as a result of advanced medical treatments and of the increasing number of immunocompromised patients.[1]

The diagnosis and the treatment of fungal infections are challenging tasks complicated by differences in patient populations and the growing variety of pathogens. Although several species of fungi are potentially pathogenic in humans *Candida*, and in particular *Candida albicans*, is the organism responsible for most of fungal diseases.[2]

Therapy against *Candida* infections relies on the use of a limited number of chemotherapeutic agents, including azoles, such as fluconazole and voriconazole, and polyenes, such as amphotericin B. Despite the fact that these molecules constitute the preferred first line therapy, the emergence and the spread of drug resistant fungal species limit their use. Today, fluconazole is poorly or not effective against mutant *Candida* species[3]. Therefore there is the need for the development of new and more active molecules, in particular active against multi-resistant species.

Chitin is an essential structural component of the fungal cell wall. Chitinases are thought to be important for fungal cell wall remodelling, and inhibition of these enzymes has been proposed as a potential strategy for development of novel antifungals. Chitin is a polymer of N-acetylglucosamine (GlcNAc) with a β-1,4 linkage between monomers. Family 18 of glycosyl hydrolases encompasses chitinases. Chitinases are the enzymes responsible for chitin degradation; they have been validated as a potential target for the design of new therapeutic agents active against fungal infections.[6-8]

Mammals are not known to synthesize chitin or to metabolize it as a nutrient, yet the human genome encodes eight well-documented genes for proteins now classified as glycoside hydrolase family18 members. Members of this family are known to adopt the TIM (triosephosphate isomerase) fold consisting of a strongly conserved $(\beta/\alpha)_8$-barrel structure. Often, separate chitin-binding domains (CBM14) are present in the carboxyl terminal region of the proteins (additional file 1: GH18 family domain structure).

The protein family includes chitinases as well as homologous proteins termed chitolectins. The latter lack the key active-site glutamate residue that donates a proton required for hydrolytic enzyme activity, but retain highly conserved residues involved in oligosaccharide binding and overall three-dimensional structure. Traditionally, chitinases are classified in two glycoside hydrolase families, GH18 and GH19, with different structures and catalytic mechanisms. Family GH18 includes the chitinases from viruses, bacteria, fungi and animals as well as classes III and V from plants. The GH19 chitinases are identified mostly in plants (classes I, II and IV), nematodes, and some bacteria. Recent data indicate chitinase activity is also present in protein families GH48 and GH20. N-acetyl-β-D-glucosaminidases such as those in family GH20 also can participate in chitin degradation by hydrolyzing GlcNAc from the non-reducing end of chito-oligosaccharides.

Although chitin itself does not exist in humans, chitinases are present in the human genome. Human chitinase family members includes acidic mammalian chitinase (AMCase). AMCase is relatively abundant in the gastrointestinal tract and is found to a lesser extent in the lung in rodents and man[10]. Recently, AMCase has been shown to be induced via a Thelper-2-specific, interleukin-13-mediated pathway in epithelial cells and macrophages in an aeroallergen asthma model and expressed in exaggerated quantities in human asthma. AMCase neutralization ameliorated Th2 inflammation and airway hyper-responsiveness. Inhibition of AMCase associated with parasitic infection decreases the recruitment of inflammatory cells and profoundly dampens T helper 2 (Th2) cellular responses in a murine model of lung inflammation, suggesting that this enzyme may be a potential target for an asthma drug therapy.[9] It has also been reported that AMCase over expression inhibits growth factor withdrawal and FasL induced epithelial cell apoptosis[11]. Both the Th2 inflammatory response and a disrupted proliferation/apoptosis cell ratio have been identified as driving mechanisms behind asthma, suggesting that this enzyme will be a promising target for an asthma drug therapy.

WO 2009/113033 relates to cyclic guanidine derivatives used as antifungal agents in particular against *Candida* species, having the general formula:

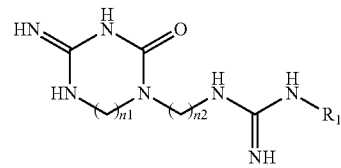

SUMMARY OF THE INVENTION

During studies on antifungal compounds, the present inventors have found that macrocyclic amidinourea derivatives were endowed with a good activity against wild-type and resistant *Candida* species.[4-5]

A new series of compounds with improved activity and a more versatile synthetic pathway, with respect to the compounds reported in Manetti et al. 2009[4] and WO 2009/113033, have been prepared.

The antifungal activity of the present compounds may be due to inhibition of the Chitinase, an enzyme that degrades the chitin wall and that is essential for the fungal cell replication and differentiation.

In the present invention a new series of amidinourea derivatives have been synthesized. These compounds have been tested against 116 clinical isolates of seven different *Candida* species (oral, vaginal, anorectal, urine, stool, blood, central venous catheter, and respiratory tract specimens) and were thus assayed against mutant *C. albicans* and *C. glabrata* strains. Such mutant strains display resistance to antifungal therapies. The compounds of the invention possess an excellent antifungal activity and they:

1) Are very active against *Candida* strains;
2) Are also active against drug resistant *Candida* strains;
3) Are potent inhibitors of chitinase, in particular of fungal chitinase.

It is an embodiment of the invention a compound having the general formula 8:

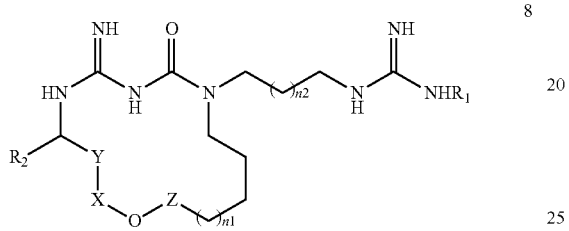

8 wherein
$n_1$ is a number from 0 to 4;
$n_2$ is a number from 1 to 7;
$R_1$ is H; linear or branched $C_1$-$C_6$ alkyl; propargyl, cyclopropylmethyl, but-2-en-1-yl, γ-methylallyl, β-methylallyl, γ,γ-dimethylallyl, benzyl, allyl, pyridin-ylmethyl; methylcarbamoyl, ethylcarbamoyl, propylcarbamoyl, or prop-2-enylcarbamoyl;
$R_2$ is H or

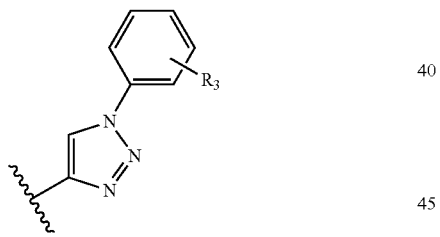

$R_3$ is OH, nitro, $NH_2$, $NHR_8$, $NR_9R_{10}$, $C_1$-$C_6$ alkyl, COOH, $CONH_2$, $CONR_{11}H$, $CONR_{12}R_{13}$, cyano, F, Cl, Br;
wherein $R_8$, $R_9$, $R_{10}$, $R_{11}$, $R_{12}$, $R_{13}$, are the same or each independently $C_1$-$C_6$ alkyl, methylcyclopropyl or propan-2-yl;
X is $CH_2$ or C(=O);
Y is $CH_2$,
or X—Y is

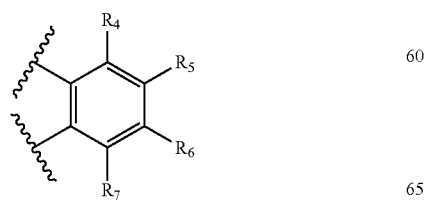

wherein $R_4$, $R_5$, $R_6$, $R_7$ are the same or each independently H, OH, nitro, $NH_2$, $NHR_{14}$, $NR_{15}R_{18}$, $C_1$-$C_6$ alkyl, COOH, $CONH_2$, $CONR_{17}H$, $CONR_{18}R_{19}$, cyano, F, Cl, Br;
wherein $R_{14}$, $R_{15}$, $R_{16}$, $R_{17}$, $R_{18}$, $R_{19}$ are the same or each independently $C_1$-$C_6$ alkyl, methylcyclopropyl or propan-2-yl;
Z is $CH_2$,

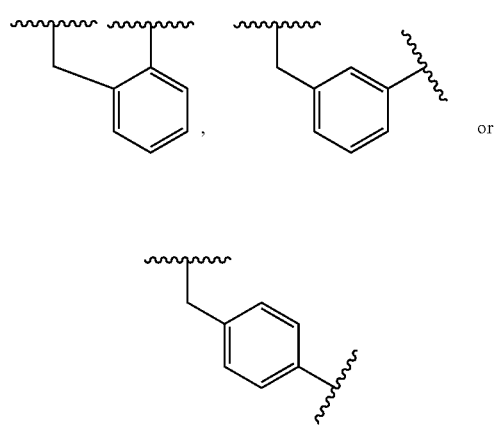

or pharmaceutically acceptable salts thereof.

Preferably the compound has formula 8 wherein $n_1$, $n_2$ and $R_1$ are as defined in claim 1;
$R_2$ is

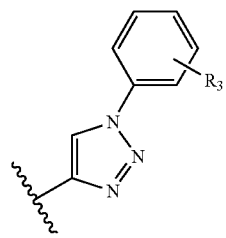

$R_3$ is as defined in claim 1;
X—Y is

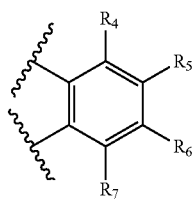

wherein $R_4$, $R_5$, $R_6$, $R_7$ are as defined above and
Z is $CH_2$ or pharmaceutically acceptable salts thereof.

Still preferably the compound has formula 8 wherein $n_1$, $n_2$ and $R_1$ are as defined above;

$R_2$ is H;
X—Y is

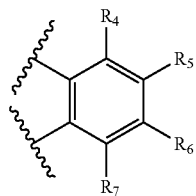

wherein $R_4$, $R_5$, $R_6$, $R_7$ are as defined above and
Z is

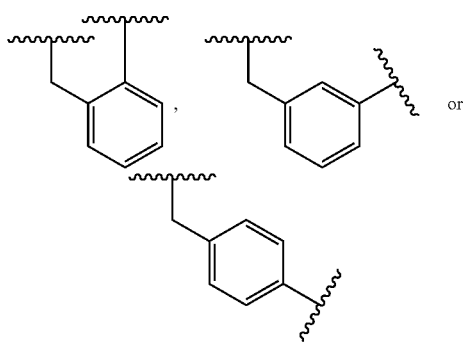

or pharmaceutically acceptable salts thereof.
Yet preferably the compound of the invention has formula 8a

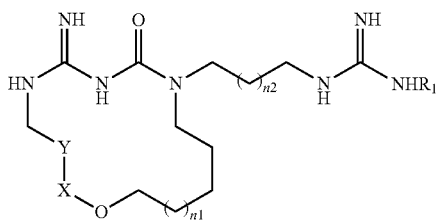

8a wherein $n_1$, $n_2$, $R_1$, X and Y are as defined above or pharmaceutically acceptable salts thereof.
In a preferred embodiment the compound has the formula 8a wherein
X—Y is

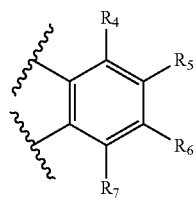

with $R_4$, $R_5$, $R_6$ and $R_7$=H or pharmaceutically acceptable salts thereof.
In a preferred embodiment the compound has the formula 8a wherein X is C(=O) and Y is $CH_2$ or pharmaceutically acceptable salts thereof.

In a yet preferred embodiment the compound is

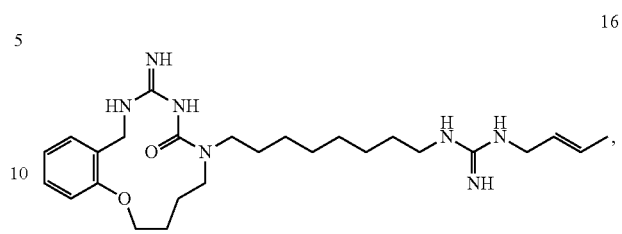

16

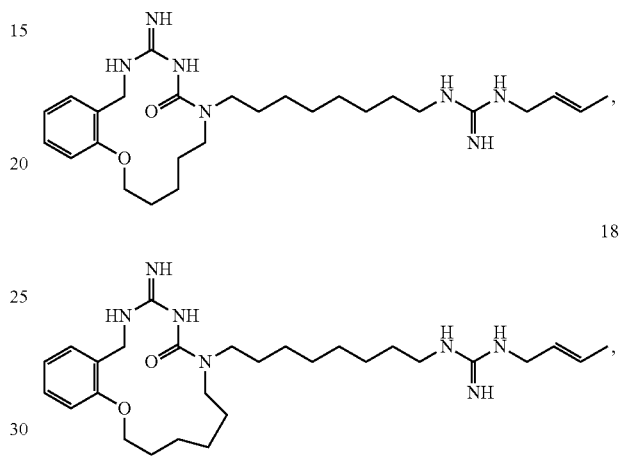

17

18

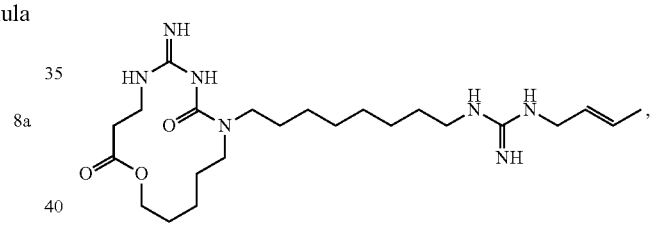

19

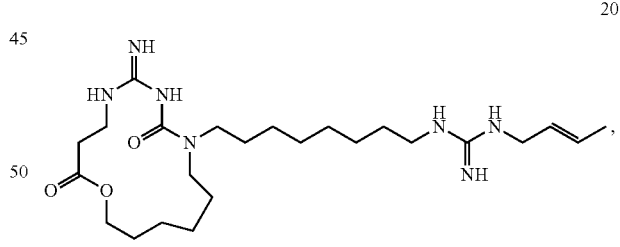

20

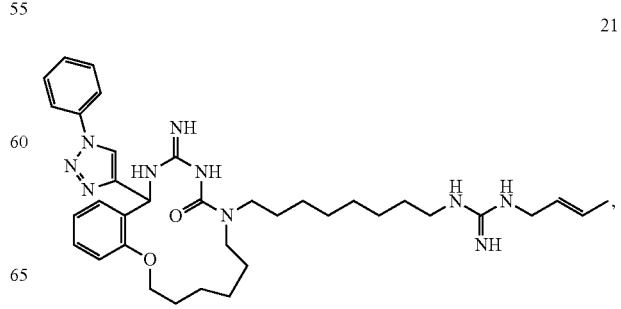

21

-continued

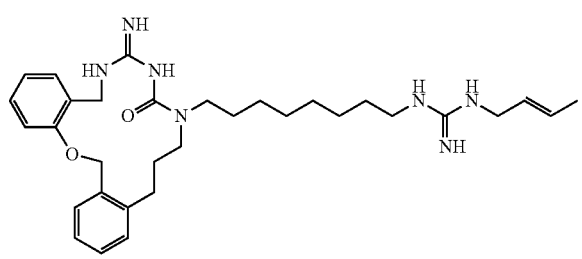

22

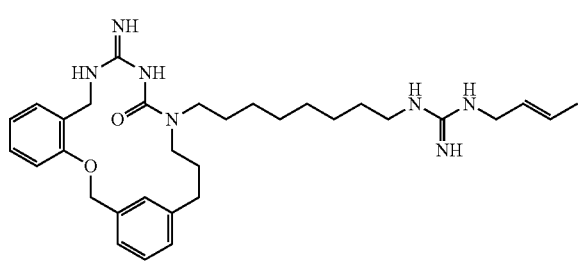

23 or pharmaceutically acceptable salts thereof.

Preferably the compounds of the invention are for medical use.

Preferably the compounds of the invention are for use as chitinase inhibitor. More preferably the chitinase belongs to the glycoside hydrolyse GH18 family of chitinases. Such GH18 family includes the chitinases from viruses, bacteria, fungi (such as of *Candida* species) and animals as well as classes III and V from plants. In particular, it includes mammalian chitinases such as acidic mammalian chitinase (AMCase).

More preferably the compounds of the invention are for use in the treatment and/or prevention of a fungal infection.

Still preferably the fungal infection is of a *Candida* species.

Yet preferably the *Candida* species is selected from the group consisting of: *C. albicans, C. guilliermondii, C. krusei, C. parapsilosis, C. tropicalis, C. kefyr* or *C. glabrata*.

More preferably the compounds of the invention are for use in the treatment and/or prevention of a fungal infection from *Candida* wherein the *Candida* species is drug resistant. The species may be resistant to any drug currently used to treat fungal infections. Preferably, the *Candida* species is resistant to fluconazole and/or voriconazole.

More preferably the compounds of the invention are for use in the treatment and/or prevention of an IL-13 and/or Th-2-mediated disease.

In one embodiment of the invention the IL-13 and/or Th-2-mediated disease is a Th-2-mediated inflammation.

In one embodiment of the invention the IL-13 and/or Th-2-mediated disease is an allergic airway disease, preferably asthma.

A further embodiment of the invention is a pharmaceutical composition comprising at least one compound of the invention as defined above and appropriate excipients or diluents.

Preferably the composition further comprises at least one therapeutic agent selected from the group consisting of: antifungal agent, anti-inflammatory agent.

More preferably the further antifungal agent is selected from the group consisting of: azole family antifungal agent (fluconazole, voriconazole), macrolides such as amphotericin, polyene antifungals such as Amphotericin B, Candicidin, Filipin, Hamycin, Natamycin, Nystatin, Rimocidin, Imidazole, triazole, and thiazole antifungals, such as for imidazoles: Canesten (clotrimazole), Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole; for triazoles: Albaconazole, Fluconazole, Isavuconazole, Itraconazole, Posaconazole, Ravuconazole, Terconazole, Voriconazole; For thiazoles: Abafungi; for allylamines: Amorolfin, Butenafine, Naftifine, Terbinafine; for echinocandins: Anidulafungin, Caspofungin, Micafungin; other antifungals may be Benzoic acid; Ciclopirox; Flucytosine; Griseofulvin; Haloprogin; Tolnaftate; Undecylenic acid; Crystal violet or Balsam of Peru.

A further embodiment of the invention is an intermediate of formula 4:

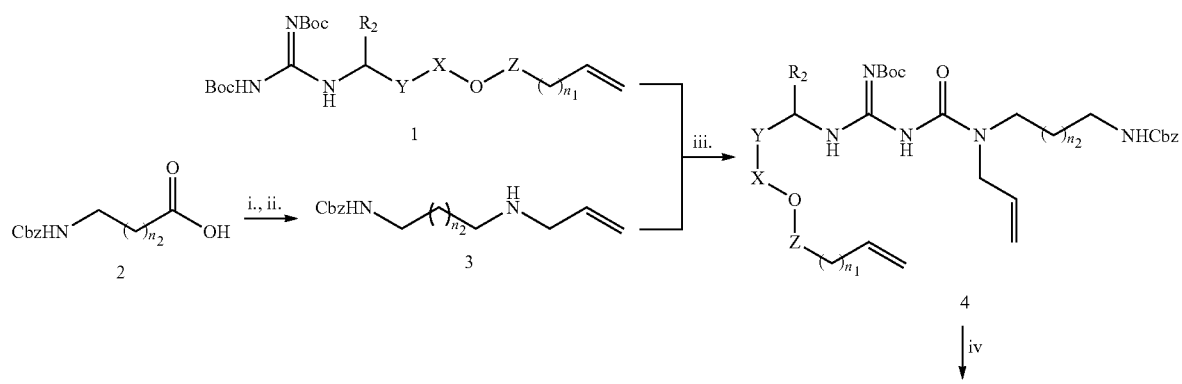

A further embodiment of the invention is a process for the preparation of a compound of formula 8 according to claim 1, said process comprising the following steps:

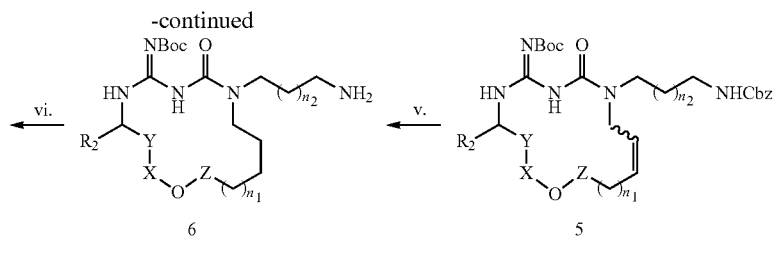
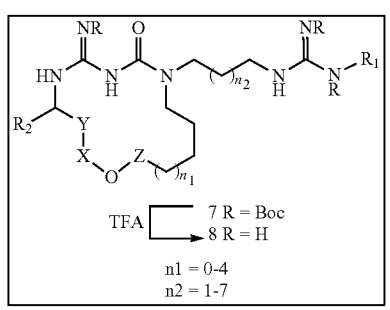

n1 = 0-4
n2 = 1-7

Reagents and Conditions:
(i) AllylNH$_2$, EDC, HOBt, DIPEA, DMF (ii) DIBAL-H, DCM, r.t. (iii) THF, reflux, 12 h (iv) Grubbs' Cat. 2nd gen., toluene or DCM 2-10 mM, 40-80° C. (v) H$_2$, Pd/C, EtOH (vi) R$_1$NBoc(C=NBoc)SMe THF, reflux, 12 h, wherein n$_1$, n$_2$, R$_1$, R$_2$, X, Y and Z are as defined above.

A further embodiment of the invention is a method for inhibiting a chitinase in a mammal comprising administering the compound of the invention as defined above in a suitable amount to the mammal in need thereof.

A further embodiment of the invention is a method for treating a fungal infection in a mammal comprising administering the compound of the invention in a suitable amount to the mammal in need thereof.

Preferably the fungal infection is of a *Candida* species.

A further embodiment of the invention is a method for treating an IL-13 and/or Th-2-mediated disease in a mammal comprising administering the compound of the invention as defined above in a suitable amount to the mammal in need thereof.

Preferably the IL-13 and/or Th-2-mediated disease is asthma.

In the present invention, the term "C$_1$-C$_6$ alkyl" refers to a straight or branched hydrocarbon chain radical, consisting solely of carbon and hydrogen atoms, having from one to six carbon atoms. suitable examples of C$_1$-C$_6$ alkyl include methyl, ethyl, n-propyl, ispropyl, butyl, tert-butyl, pentyl, and hexyl.

in the present invention by "drug resistent" or "drug resistance" it is meant the ability of resist to antifungal drugs or compounds currently on the market, in particular drugs belonging to the azole family, such as fluconazole and voriconazole, and macrolides such as amphotericin. resistance may be also to other antifungal agents such as polyene antifungals such as Amphotericin B, Candicidin, Filipin, Hamycin, Natamycin, Nystatin, Rimocidin, Imidazole, triazole, and thiazole antifungals, such as for imidazoles: Canesten (clotrimazole), Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole; for triazoles: Albaconazole, Fluconazole, Isavuconazole, Itraconazole, Posaconazole, Ravuconazole, Terconazole, Voriconazole; For thiazoles: Abafungi; for allylamines: Amorolfin, Butenafine, Naftifine, Terbinafine; for echinocandins: Anidulafungin, Caspofungin, Micafungin; other antifungals may be Benzoic acid; Ciclopirox; Flucytosine; Griseofulvin; Haloprogin; Tolnaftate; Undecylenic acid; Crystal violet or Balsam of Peru.

Pharmaceutically acceptable salts comprise conventional non-toxic salts obtained by salification of a compound of formula 8 or 8a with inorganic acids (e.g. hydrochloric, hydrobromic, sulphuric, or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc, New York 1996, Volume 13, page 453-497. Other salts, which are not pharmaceutically acceptable, for example the trifluoroacetate salt, may be useful in the preparation of compounds of this invention and these form a further aspect of the invention. The invention includes within its scope all possible stoichiometric and non-stoichiometric forms of the salts of the compounds of formula 8 or 8a.

In addition, the compounds of formula 8 or 8a may exist in unsolvated as well as in solvated forms with pharmaceutically acceptable solvents such as water, EtOH and the like.

Certain compounds of formula 8 or 8a may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula 8 or 8a as mixtures with isomers thereof in which one or more chiral centres are inverted.

The invention also includes all suitable isotopic variations of a compound of the invention. Examples of isotopes that can be incorporated into compounds of the invention include isotopes such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the invention, for example, those in which a radioactive isotope such as $^3$H or $^{14}$C is incorporated, are useful in drug and/or substrate tissue distribution studies. Further, substitution with isotopes such as deuterium $^2$H, may afford certain therapeutic advantages resulting from greater metabolic stability. Isotopic variations of the compounds of the invention can generally be prepared by conventional procedures such as by the illustrative methods or by the preparations described in the examples hereafter using appropriate isotopic variations of suitable reagents.

Considering the role of chitinase in Th2 cellular responses, in particular in interleukin-13 mediated pathways, the compounds of the invention are also useful in the prevention and/or treatment of IL-13 and/or Th2-mediated pathologies or diseases[9 and 11].

The compounds of formula 8 or 8a can also be used in combination with additional agents, in particular anti-fungal agents, either by separate administrations, or by including the two active principles in the same pharmaceutical formulation. Non-exhaustive examples of suitable additional agents are as defined below.

The invention also provides pharmaceutical compositions comprising one or more compounds of this invention and one or more pharmaceutically acceptable excipient and/or diluent. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable, or infusible liquid solutions, suspensions, suppositories, preparation for inhalation.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene to make up the daily dose. The determination of optimum dosages for a particular patient is well known to one skilled in the art. glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Typical transdermal formulations comprise conventional aqueous and non-aqueous vectors, such as creams, oils, lotions or pastes or can be in the form of membranes or medicated patches.

A reference for the formulations is the book by Remington ("Remington: The Science and Practice of Pharmacy", Lippincott Williams & Wilkins, 2000).

The compounds of the present invention may be employed alone as a sole therapy or in combination with other therapeutic agents for the treatment of the above-mentioned conditions.

The other therapeutic agents may be antifungal drugs or compounds currently on the market, in particular drugs belonging to the azole family, such as fluconazole and voriconazole, and macrolides such as amphotericin. Other antifungal agents comprise polyene antifungals such as Amphotericin B, Candicidin, Filipin, Hamycin, Natamycin, Nystatin, Rimocidin, Imidazole, triazole, and thiazole antifungals, such as for imidazoles: Canesten (clotrimazole), Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole; for triazoles: Albaconazole, Fluconazole, Isavuconazole, Itraconazole, Posaconazole, Ravuconazole, Terconazole, Voriconazole; For thiazoles: Abafungi; for allylamines: Amorolfin, Butenafine, Naftifine, Terbinafine; for echinocandins: Anidulafungin, Caspofungin, Micafungin; other antifungals may be Benzoic acid; Ciclopirox; Flucytosine; Griseofulvin; Haloprogin; Tolnaftate; Undecylenic acid; Crystal violet or Balsam of Peru.

The combination can be administered as separate compositions (simultaneous, sequential) of the individual components of the treatment or as a single dosage form containing both agents. When the compounds of this invention are in combination with others active ingredients, the active ingredients may be separately formulated into single-ingredient preparations of one of the above-described forms and then provided as combined preparations, which are given at the same time or different times, or may be formulated together into a two- or more-ingredient preparation.

Compounds of general formula 8 or 8a may be administered to a patient in a total daily dose of, for example, from 0.001 to 1000 mg/kg body weight daily. Dosage unit compositions may contain such amounts of submultiples thereof As is common practice, the compositions are normally accompanied by written or printed instructions for use in the treatment in question.

The following examples and biological data are presented in order to further illustrate the invention.

It is further object of the invention a process for the preparation of a compound as disclosed in any of claim 1 comprising the following steps:

a) Reaction of a compound of general formula 1 with a compound of general formula 3

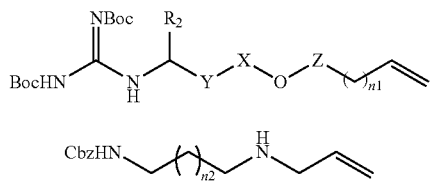

b) Intramolecular reaction of guanidinic diene of general structure 4,

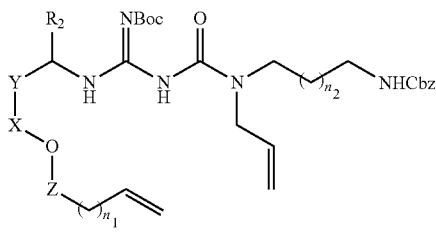

DETAILED DESCRIPTION OF THE INVENTION

Chemistry

The compounds having formula 8 described in the invention can be synthesized as described in scheme 1 below:

Reagents and Conditions:
(i) AllylNH$_2$, EDC, HOBt, DIPEA, DMF (ii) DIBAL-H, DCM, r.t. (iii) THF, reflux, 12 h (iv) Grubbs' Cat. 2nd gen., toluene or DCM 2-10 mM, 40-80° C. (v) H$_2$, Pd/C, EtOH (vi) R$_1$NBoc(C=NBoc)SMe, THF, reflux, 12 h.

Wherein $n_1$, $n_2$, $R_1$, $R_2$, X, Y and Z are as defined herein above.

Unless otherwise indicated, commercially available reagents and solvents were used without further purification. Specifically, the following abbreviations may have been used in the descriptions of the experimental methods:

min: minutes; h: hour(s); r.t.: room temperature, NMR: Nuclear Magnetic Resonance;

MHz: Megahertz; $^1$H: proton; $^{13}$C: carbon 13; mg: milligrams; mmol: millimoles; mL: milliliters; μL: microliters; N: Normal;

NMR Nuclear Magnetic Resonance; LC-MS Liquid Chromatography Mass Spectrum; TMS: tetramethylsilane; THF: tetrahydrofuran; Tf: trifluoromethylsulfonyl; Boc: tert-butyloxycarbonyl; DCM: dichloromethane; EtOAc: ethyl acetate; EDC: N-(3-Dimethylaminopropyl)-N'-ethylcarbodiimide hydrochloride; HOBT: 1-Hydroxybenzotriazole; DMF: N,N-dimethylformamide; DIPEA: N,N'-Diisopropylethylamine; DIBAL-H: Diisobutylaluminium hydride; MeOH: methyl alcohol; MeOD: deuterated methyl alcohol; EtOH: ethyl alcohol; Et$_2$O: diethyl ether; Et$_3$N: triethylamine; DMSO: dimethyl sulfoxide; CbzCl: Benzyl Chloroformate; EP: Petroleum ether; DCC: N,N'-dicyclohexyl methanediimine; TMSCI: Trimethylsilyl chloride; Py: pyridine.

Except where indicated otherwise, all temperatures are expressed in ° C. (degrees centigrade) or K (Kelvin).

The structure of the intermediates and of the final compounds of the synthesis were confirmed by NMR and/or LC-MS analysis.

The $^1$H-NMR spectra were acquired with a Varian Gemini 200 (200 MHz) or with a Brucker Avance DPX400 (400 MHz).

Scheme 1

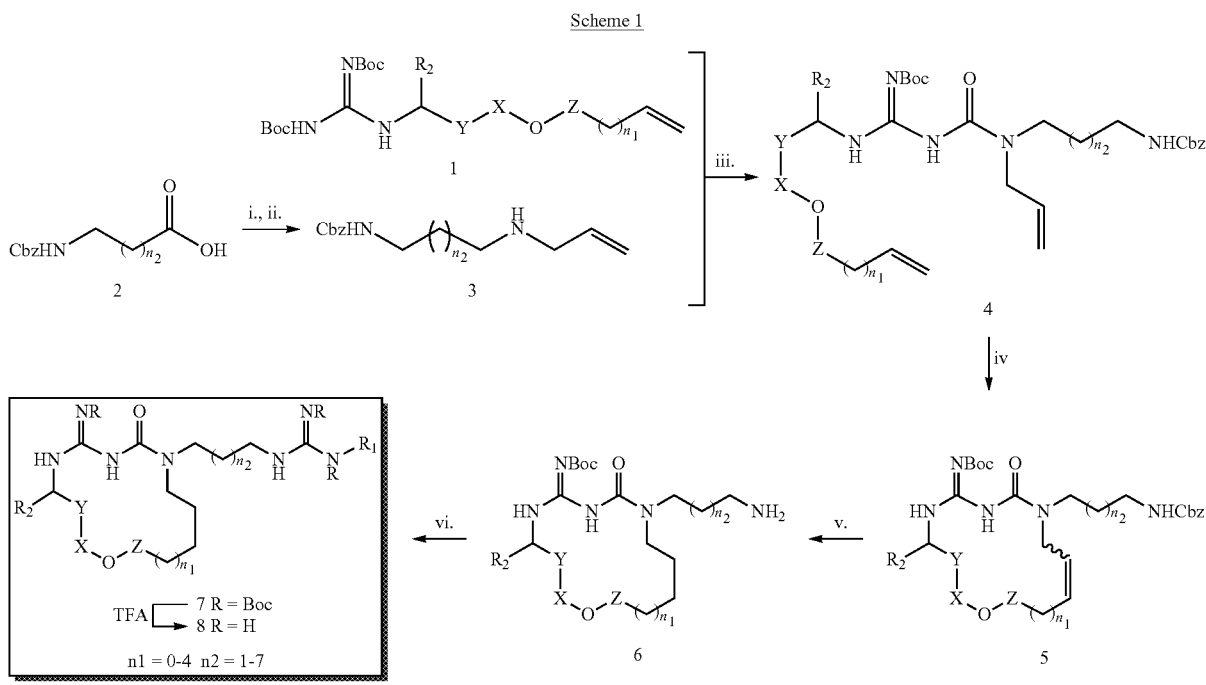

The $^{13}$C-NMR spectra were acquired with a Brucker Avance DPX400 (400 MHz).

The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet).

The LC-MS analyses were carried out on a system consisted of a Varian apparatus (Varian Inc) including a vacuum solvent degassing unit, two pumps (212-LC), a Triple Quadrupole MSD (Mod. 320-LC) mass spectrometer with ES interface and Varian MS Workstation System Control Vers. 6.9 software. Chromatographic separation was obtained using a Pursuit C18 column (50×2.0 mm) (Varian) with 3 μm particle size and gradient elution: eluent A being CH$_3$CN and eluent B consisting of an aqueous solution of formic acid (0.1%). The analysis started with 0% of eluent A, which was linearly increased up to 50% in 10 min, then slowly increased up to 60% up to 15 min. The flow rate was 0.3 ml/min and injection volume was 5 μL. The instrument operated in positive mode and parameters were: detector 1850 V, drying gas pressure 25.0 psi, desolvation temperature 300.0° C., nebulizing gas 45.0 psi, needle 5000 V and shield 600 V. Nitrogen was used as nebulizer and drying gas. Collision induced dissociation was performed using Argon as the collision gas at a pressure of 1.8 mTorr in the collision cell, the collision energy was set to 149 eV. Three transitions were recorded at 279.8 (m/z), 321.9 (m/z) and 368.0 (m/z) setting capillary voltage to −27.5 V, −23.5 V and −19.5 V respectively.

Example 16

For reasons of clarity, the detailed synthesis of example 16 has been reported in scheme 2 below.

The yields were calculated assuming that products were 100% pure if not stated otherwise.

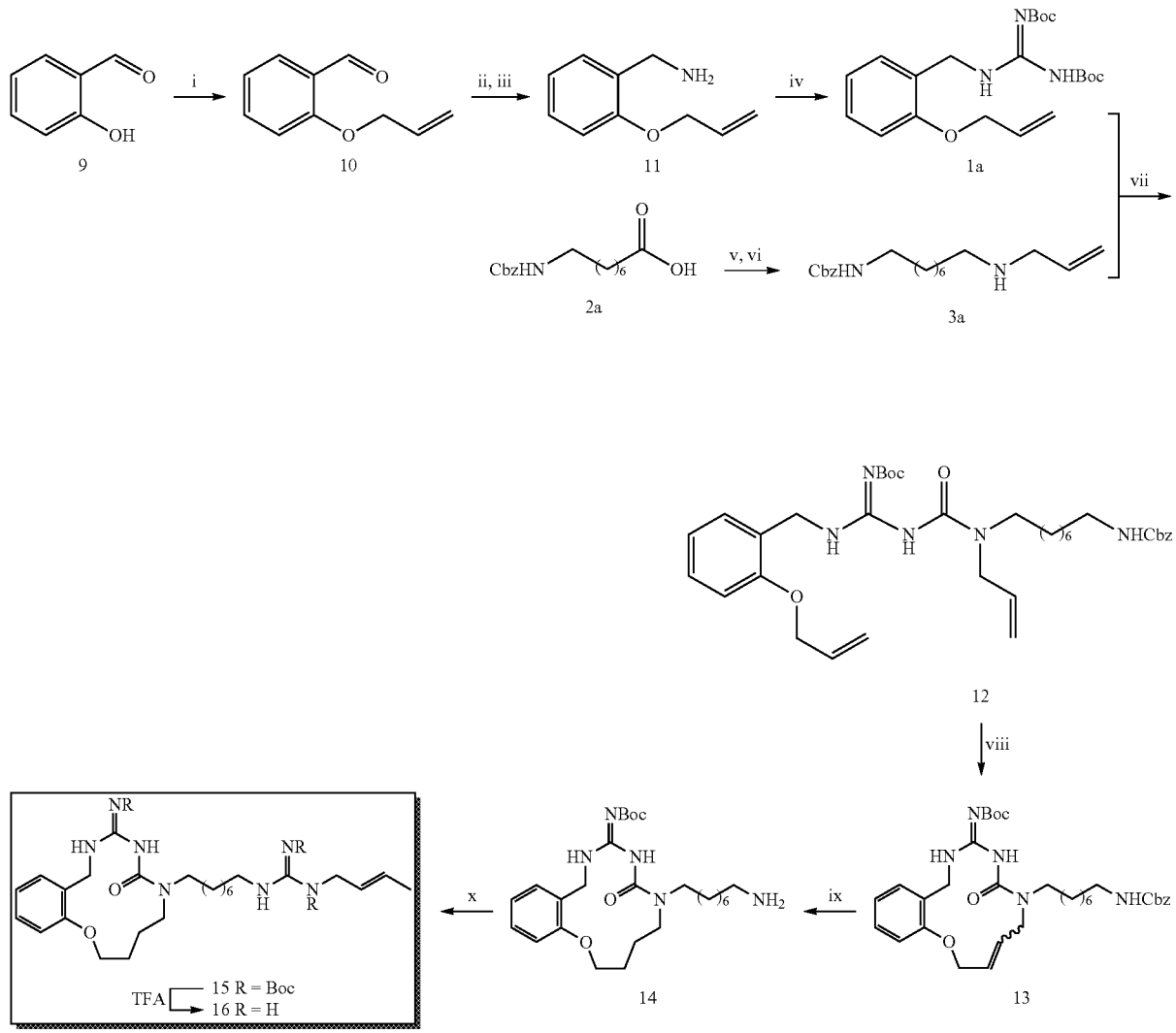

Scheme 2 Experimental procedures for the synthesis of example 16

Reagents and Conditions:

(i) BrCH$_2$CH=CH$_2$, K$_2$CO$_3$, DCM, reflux (ii) NH$_2$OH, Py, EtOH, reflux (iii) Zn, HCl, THF, reflux (iv) (BocNH)$_2$C=NTf, Et$_3$N, DCM (v) AllylNH$_2$, EDC, HOBt, DIPEA, DMF (vi) DIBAL-H, DCM, r.t. (vii) THF, reflux, 12 h (viii) Grubbs' Cat. 2nd gen., toluene or DCM 2-10 mM, 40-80° C. (ix) H$_2$, Pd/C, EtOH (x) CrotylNBoc(C=NBoc)SMe, THF, reflux, 12 h Procedure for the Preparation of
2-prop-2-enoxybenzaldehyde 10

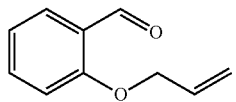

10

2-hydroxybenzaldehyde 9 (0.5 ml, 4.69 mmol, Sigma-Aldrich catalogue id: S356) was dissolved in CH$_3$CN (10 ml) and K$_2$CO$_3$ (0.97 ml, 7.03 mmol) and 3-bromoprop-1-ene (0.45 ml, 5.16 mmol, Sigma-Aldrich catalogue id: 337528) were added. Mixture was stirred at reflux for 12 hours. Solvent was then evaporated in vacuum and the residue dissolved in EtOAc (5 mL). Water (10 ml) was added and the mixture stirred for 10 min at room temperature. Organic phase was then separated and the aqueous layer was extracted with EtOAc (2×10 ml). The combined organic phases were dried over Na$_2$SO$_4$, filtered and concentrated under reduced pressure to give title compound 10.

Yield 99%. $^1$H NMR (400 MHz, CDCl$_3$) δ=10.25 (1H, s), 7.54-7.52 (1H, m), 7.23-7.19 (1H, m), 6.72-6.66 (2H, m), 5.82-5.75 (1H, m), 5.20-5.15 (1H, d, J=17.6 Hz), 5.05-5.03 (1H, d, J=10.8 Hz), 4.33-4.31 (2H, m) ppm.

$^{13}$C NMR (CDCl$_3$) δ 188.9, 160.6, 135.6, 132.2, 127.8, 124.7, 120.5, 117.5, 112.7, 68.7 ppm.

Liquid chromatography Mass Spectroscopy (LCMS) m/z (ES+) m/z: 347.0 [2M+Na]$^+$, 185.0 [M+Na]$^+$, 163.0 [M+H]$^+$.

Elemental analysis for C$_{10}$H$_{10}$O$_2$: Calcd. C, 74.06; H, 6.21. Found C, 74.36; H, 6.52.

Procedure for the Preparation of
(2-prop-2-enoxyphenyl)methanamine 11

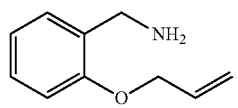

11

2-prop-2-enoxybenzaldehyde 10 (4.69 mmol) was dissolved in EtOH (10 ml) and pyridine (0.45 ml, 5.63 mmol) and NH$_2$OH (490 mg, 7.03 mmol) were added. The mixture was heated at reflux for 2 h. Brine was added, the aqueous layer was extracted with EtOAc (2×10 ml) and the combined organic phases were dried over Na$_2$SO$_4$ and filtered. The solvent was evaporated under reduced pressure, and the residue was purified by flash chromatography (SiO$_2$) using hexane-Et$_2$O, 3:1 as the eluent affording a mixture of E/Z isomers of oxime.

N-[(2-prop-2-enoxyphenyl)methylidene]hydroxylamine (818 mg, 4.62 mmol) was dissolved in THF (30 ml) and Zn (3.00 g, 46.23 mmol) was added. HCl 2N (12 ml) was added and mixture was stirred at reflux for 3 h. The reaction mixture was cooled to room temperature, filtered on a celite pad to remove the excess zinc and condenser under reduced pressure. pH was adjusted to >10 by addition of ammonium hydroxide. The aqueous layer was extracted with EtOAc (2×10 ml) and the combined organic phases were dried over Na$_2$SO$_4$ and filtered. The solvent was evaporated under reduced pressure to give title compound 11.

Yield 99%. $^1$H NMR (400 MHz, CDCl$_3$) δ=7.06-7.01 (2H, m), 6.77-6.73 (1H, m), 6.67-6.65 (1H, m), 5.92-5.84 (1H, m), 5.28-5.24 (1H, d, J=17.2 Hz), 5.13-5.10 (1H, d, J=10.4 Hz), 4.36-4.35 (2H, m), 3.70-3.68 (2H, m), 1.65 (2H, br s) ppm.

$^{13}$C NMR (CDCl$_3$) δ 156.1, 133.2, 131.9, 128.2, 127.7, 120.5, 116.8, 111.3, 68.3, 42.4 ppm.

LCMS m/z (ES+) m/z=349.0 [2M+Na]$^+$, 202.0 [M+Na]$^+$, 163.9 [M+H]$^+$.

Elemental analysis for C$_{10}$H$_{13}$NO: Calcd. C, 73.59; H, 8.03; N, 8.58. Found C, 73.86; H, 8.47; N, 9.01.

Procedure for the Preparation of tert-butyl N-({[(tert-butoxy)carbonyl]amino}(trifluoromethanesulfonylimino)methyl)carbamate (also named as 1,3-Di-Boc-2-(trifluoromethylsulfonyl)guanidine)

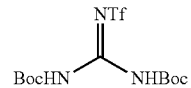

Tert-butyl N—[N-[(2-methylpropan-2-yl)oxycarbonyl]carbamimidoyl]carbamate (7.12 g, 27.45 mmol, Sigma-Aldrich catalogue id: 496871) was dissolved in dry DCM (136 ml) and Et$_3$N (4.2 ml, 30.19 mmol) was added. The solution was cooled at −78° C. and trifluoromethylsulphonyl trifluoromethanesulphonate (Sigma-Aldrich, catalogue ID: 91737) solution 1 M in methylene chloride (35.68 ml) was added in one portion. The mixture was then allowed to warm to r.t. and stirred for 4 h. Water was added to the mixture and organic layers were washed two times with brine while aqueous phase was extracted twice with EtOAc. Finally combined organic phases were dried over Na$_2$SO$_4$, filtered and evaporated in vacuum. The solid residue was recrystallized from hexane led to the title compound tert-butyl N-({[(tert-butoxy)carbonyl]amino}(trifluoromethanesulfonylimino)methyl)carbamate (also named as 1,3-Di-Boc-2-(trifluoromethylsulfonyl)guanidine).

Yield 70%. $^1$H NMR (400 MHz, CDCl$_3$) δ=8.00 (2H, s), 1.4 (18H, m) ppm.

$^{13}$C NMR (CDCl$_3$) δ 151.0, 148.0, 117.5, 85.9, 27.7 ppm.

LCMS m/z (ES+) m/z=805.0 [2M+Na]$^+$, 414.0 [M+Na]$^+$, 391.9 [M+H]$^+$.

Elemental analysis for C$_{12}$H$_{20}$F$_3$N$_3$O$_6$S: Calcd. C, 36.83; H, 5.15; N, 10.74. Found C, 37.13; H, 5.35; N, 10.94.

Procedure for the Preparation of tert-butyl N-[[(2-methylpropan-2-yl)oxycarbonylamino]-[(2-propoxyphenyl)methylamino]methyl]carbamate 1a

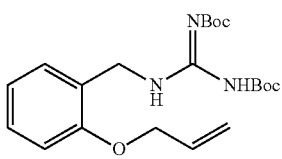

1a (2-prop-2-enoxyphenyl)methanamine 11 (345 mg, 2.1 mmol), Et$_3$N (0.58 ml, 4.2 mmol) and 1,3-Di-Boc-2-(trifluoromethylsulfonyl)guanidine were mixed in DCM (25 ml) and mixture stirred at room temperature overnight. The aqueous layer was separated and extracted with EtOAc (2×10 ml) and the combined organic phases were dried over Na$_2$SO$_4$ and filtered. The solvent was evaporated under reduced pressure, and the residue was purified by flash chromatography (hexane-Et$_2$O, 8:2) affording guanidine title compound 1a.

Yield 75%. $^1$H NMR (400 MHz, CDCl$_3$) δ=11.42 (1H, s), 8.62 (1H, s), 7.09-7.07 (1H, d, J=7.6 Hz), 7.03-6.99 (1H, m), 6.71-6.63 (2H, m), 5.92-5.83 (1H, m), 5.22-5.18 (1H, d, J=17.6 Hz), 5.06-5.04 (1H, d, J=10.4 Hz), 4.46-4.45 (2H, m), 4.37-4.35 (2H, m), 1.31 (9H, s), 1.26 (9H, s) ppm.

$^{13}$C NMR (CDCl$_3$) δ 163.4, 156.4, 155.8, 152.9, 132.9, 129.4, 128.7, 125.5, 120.4, 117.1, 111.3, 82.3, 78.5, 68.5, 40.6, 28.0, 27.7 ppm.

LCMS m/z (ES+) m/z=833.0 [2M+Na]$^+$, 428.0 [M+Na]$^+$, 406.2 [M+H]$^+$.

Elemental analysis for C$_{21}$H$_{13}$N$_3$O$_5$: Calcd. C, 62.20; H, 7.71; N, 10.36. Found C, 62.56; H, 7.92; N, 10.85.

Procedure for the Preparation of 8-(benzyloxycarbonylamino)octanoic acid 2a

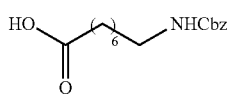

2a 8-aminooctanoic acid (500 mg, 3.14 mmol, Sigma-Aldrich catalogue ID: 855294) and K$_2$CO$_3$ (867 mg, 6.28 mmol) were dissolved in THF (15 ml) (suspension). Then CbzCl (0.67 ml, 4.71 mmol) was added and the mixture was stirred at r.t. overnight.

The reaction was quenched with EtOAc and H$_2$O. Aqueous phase was separated and pH of aqueous phase was adjusted to pH=2 by addition of HCl 4N and extracted twice with EtOAc. Combined organic phase were then dried over Na$_2$SO$_4$, filtered and evaporated in vacuum affording the title compound 2a.

Yield 99%. $^1$H NMR (400 MHz, CDCl$_3$) δ 11.01 (1H, s), 7.28-7.19 (5H, m), 5.11-5.07 (1H, d, J=16 Hz), 5.05-5.03 (1H, d, J=8 Hz), 3.18-3.16 (2H, m), 2.44-2.40 (2H, m), 1.64-1.62 (2H, m), 1.48-1.43 (2H, m), 1.32 (6H, m) ppm.

$^{13}$C NMR (CDCl$_3$) δ 178.7, 156.4, 136.5, 128.4, 128.0, 128.0, 66.5, 41.4, 33.8, 29.7, 28.6, 26.4, 24.7 ppm.

LCMS m/z (ES+) m/z=609.0 [2M+Na]$^+$, 316.0 [M+Na]$^+$, 294.1 [M+H]$^+$.

Elemental analysis for C$_{16}$H$_{23}$NO$_4$: Calcd. C, 65.51; H, 7.90; N, 4.77. Found C, 65.96; H, 8.35; N, 5.04.

Procedure for the Preparation of benzyl N-[8-oxo-8-(prop-2-enylamino)octyl]carbamate

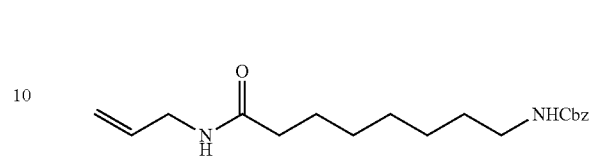

The 8-(benzyloxycarbonylamino)octanoic acid 2a (14 mmol), HOBT (424 mg, 3.14 mmol), EDC (487 mg, 3.14 mmol), DIPEA (0.66 ml, 3.77 mmol), allylamine (0.23 ml, 3.14 mmol) were mixed in DMF (5 ml). Mixture was stirred overnight at room temperature. The reaction was quenched with NaHCO$_3$, and then aqueous phase was separated and extracted with EtOAc (3×5 ml). The solvent was evaporated under reduced pressure, and the residue was purified by flash chromatography (EtOAcEP, 4:1) affording benzyl N-[8-oxo-8-(prop-2-enylamino)octyl]carbamate.

Yield 75%. $^1$H NMR (400 MHz, CDCl$_3$) δ 7.28-7.19 (5H, m), 5.79-5.70 (1H, m), 5.74 (1H, br s), 5.11-5.07 (1H, d, J=17.2 Hz), 5.03-5.01 (1H, d, J=10.4 Hz), 5.00 (2H, s), 4.78 (1H, br s), 3.81-3.78 (2H, t, J=4.8 Hz), 3.10-3.08 (2H, m), 2.12-2.08 (2H, t, J=7.6 Hz), 1.55 (2H, m), 1, 40 (2H, m), 1.23-1.18 (8H, m) ppm.

$^{13}$C NMR (CDCl$_3$) δ 172.8, 156.3, 136.5, 134.2, 128.4, 127.9, 127.6, 116.9, 66.4, 41.7, 40.8, 36.4, 29.7, 28.9, 28.7, 26.3, 25.4 ppm.

LCMS m/z (ES+) m/z=687.0 [2M+Na]$^+$, 355.0 [M+Na]$^+$, 333.1 [M+H]$^+$.

Elemental analysis for C$_{19}$H$_{28}$N$_2$O$_3$: Calcd. C, 68.65; H 8.49; N 8.43. Found C, 69.06; H, 8.95; N, 8.93.

Procedure for the Preparation benzyl N-[8-(prop-2-enylamino)octyl]carbamate 3a

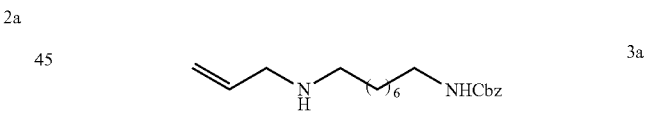

3a benzyl N-[8-oxo-8-(prop-2-enylamino)octyl]carbamate (747 mg, 2.25 mmol) was dissolved in CH$_2$Cl$_2$ dry (5 ml) and cooled at −78° C. DIBAL (3.37 ml, 3.37 mmol) was added and mixture was stirred 1 h at −78° C. then mixture was warmed at room temperature DIBAL (4.5 ml, 4.5 mmol) was added again and mixture was stirred for ⅔ h. The reaction was quenched with EtOAc and Rochelle salt. The crude title compound 3a was used in the next step.

Yield 99%. $^1$H NMR (400 MHz, CDCl$_3$) δ=7.28-7.19 (5H, m), 5.79-5.70 (1H, m), 5.11-5.07 (1H, d, J=17.2 Hz), 5.03-5.01 (1H, d, J=10.4 Hz), 5.00 (2H, s), 3.22-3.20 (2H, m), 2.09-2.05 (4H, m), 1.40-1.50 (4H, m), 1.23-1.18 (8H, m) ppm.

$^{13}$C NMR (CDCl$_3$) δ 156.3, 141.2, 134.2, 129.0, 128.1, 127.9, 116.0, 65.0, 52.1, 49.8, 41.9, 31.0, 29.9, 29.4, 27.0, 26.8 ppm.

LCMS m/z (ES+) m/z=659.0 [2 M+Na]$^+$, 341.0 [M+Na]$^+$, 319.0 [M+H]$^+$.

Procedure for the Preparation of benzyl N-[8-[[N'-[(2-methylpropan-2-yl)oxycarbonyl]-N-[(2-prop-2-enoxyphenyl)methyl]carbamimidoyl]carbamoyl-prop-2-enylamino]octyl]carbamate 12

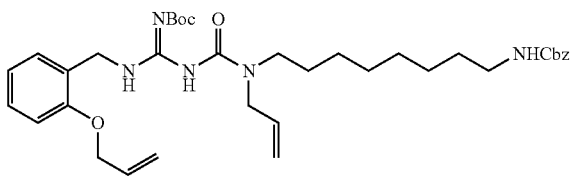

tert-butyl N-[[(2-methylpropan-2-yl)oxycarbonylamino]-[(2-propoxyphenyl)methylamino]methyl]carbamateBenzyl 8-(allylamino) octylcarbamate 1a (2.25 mmol) and compound 3a (1.4 mmol) were mixed in THF (10 ml), Et$_3$N (1.4 mmol) was added and mixture was refluxed overnight. Solvent was removed and the residue was purified by flash chromatography (hexane-Et$_2$O from 9:1 to 1:1) affording the title compound 12.

Yield 80%. $^1$H NMR (400 MHz, CDCl$_3$) δ 12.27 (1H, s), 8.47 (1H, s), 7.26-7.21 (5H, m), 7.18-7.12 (2H, m), 6.83-6.76 (2H, m), 6.05-5.97 (1H, m), 5.75-5.67 (1H, m), 5.36-5.32 (1H, d, J=17.2 Hz), 5.21-5.18 (1H, d, J=10.4 Hz), 5.07-5.01 (1H, m), 5.00-4.99 (2H, m), 4.98-4.96 (1H, m), 4.52-4.47 (4H, m), 3.86-3.84 (2H, m), 3.37-3.33 (1H, m), 3.18-3.14 (1H, m), 3.09-3.06 (2H, m), 1.43 (4H, m), 1.37 (9H, m), 1.21-1.16 (8H, m) ppm.

$^{13}$C NMR (CDCl$_3$) δ 163.6, 156.3, 153.9, 153.1, 136.7, 135.3, 134.6, 129.2, 128.8, 128.2, 128.0, 127.8, 127.0, 120.4, 117.1, 115.4, 111.4, 81.7, 68.6, 66.1, 50.3, 48.3, 40.9, 40.2, 29.8, 29.2, 28.5, 27.9, 27.8, 26.8, 26.5 ppm.

LCMS m/z (ES+) m/z=672.3.0 [M+Na]$^+$, 688.2 [M+K]$^+$, 650.3 [M+H]$^+$.

Elemental analysis for C$_{36}$H$_{51}$N$_5$O$_6$: Calcd. C, 66.54; H, 7.91; N, 10.78. Found C, 66.93; H, 8.11; N, 10.98.

Procedure for the Preparation of benzyl N-[8-[4-[(2-methylpropan-2-yl)oxycarbonylimino]-6-oxo-12-oxa-3,5,7-triazabicyclo[11.4.0]heptadeca-1(13),9,14,16-tetraen-7-yl]octyl]carbamate 13

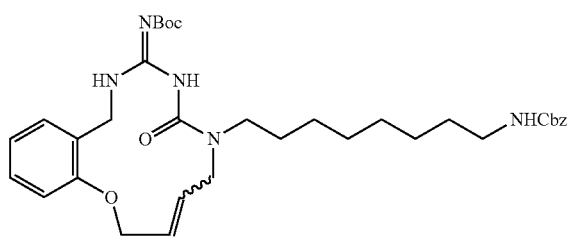

The next step is a ring closing metathesis and was made by two different procedures:

A. The starting material compound 12 (0.43 mmol) was dissolved in DCM (solution 2 mM); second generation Grubbs catalyst (0.043 mmol, Sigma-Aldrich catalogue ID: 569747) was dissolved in 2 ml of DCM and added to previous solution via syringe pump over 4 h at 40/50° C. The solvent was evaporated under reduced pressure, and the residue was purified by flash chromatography (hexane-Et$_2$O, 9:1) affording the title compound 13.

B. The starting material compound 12 (0.76 mmol) was dissolved in toluene (solution 10 mM); Grubbs catalyst (0.15 mmol) was dissolved in 2 ml of toluene and added to previous solution via syringe pump over 4 h at 100° C. The solvent was evaporated under reduced pressure, and the residue was purified by flash chromatography (hexane-Et$_2$O, 9:1) affording the title compound 13.

Procedure B; Yield 30%. $^1$H NMR (400 MHz, CDCl$_3$) δ 7.33-7.16 (5H, m), 7.02-7.89 (4H, m), 5.38-5.32 (2H, m), 5.07-5.05 (2H, m), 4.65-4.45 (4H, m), 3.80-3.70 (2H, m), 3.17-3.14 (4H, m), 1.43 (9H, m), 1.26 (12H, m) ppm.

$^{13}$C NMR (CDCl$_3$) δ 163.8, 156.3, 155.3, 153.4, 152.9, 136.6, 129.8, 129.3, 128.7, 128.4, 121.6, 113.4, 82.0, 75.0, 66.4, 48.1, 46.3, 41.0, 29.8, 29.3, 29.1, 28.6, 28.0, 26.9, 26.5, 24.6 ppm.

LCMS m/z (ES+) m/z=660.3[M+Na]$^+$, 688.2 [M+K]$^+$, 622.3 [M+H]$^+$.

Elemental analysis for C$_{34}$H$_{47}$N$_5$O$_6$: Calcd. C, 65.68; H, 7.62; N, 11.26; O, 15.44. Found C, 65.98; H, 7.91; N, 11.72; O, 15.83.

Procedure for the Deprotection of tert-butyl N-[7-(8-aminooctyl)-6-oxo-12-oxa-3,5,7-triazabicyclo[11.4.0]heptadeca-1(13),14,16-trien-4-ylidene]carbamate 14

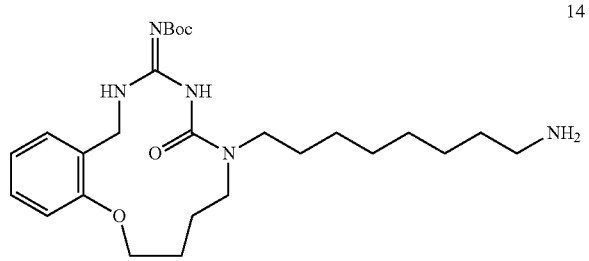

Compound 13 (0.097 mmol) was diluted in EtOH (9 ml) and Pd/C, 10% wt. (45 mg) was added. H$_2$ was insufflated and the mixture was stirred for 5 h. The reaction mixture was filtered through celite and then solvent was evaporated in vacuum. Crude title compound 14 was used in the next step without any further purification.

Yield 99%. $^1$H NMR (400 MHz, CDCl$_3$) δ=7.27-7.08 (2H, m), 6.88-6.77 (2H, m), 4.61-4.60 (2H, m), 4.02-3.98 (2H, m), 3.30-3.26 (4H, m), 3.14-3.10 (2H, m), 1.76-1.75 (2H, m), 1.59-1.54 (6H, m), 1.43 (9H, m), 1.20-1.14 (8H, m) ppm LCMS m/z (ES+) m/z=512.3[M+Na]$^+$, 528.2 [M+K]$^+$, 490.3 [M+H]$^+$.

Procedure for the Preparation of tert-butyl N-but-2-enyl-N—[N'-[(2-methylpropan-2-yl)oxycarbonyl]-N-methylsulfanylcarbamimidoyl]carbamate

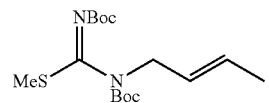

To a stirred suspension of KOH (2.8 mmol) in a solution of $CH_2Cl_2/CH_3CN$ (19:1, 3.5 mL), Tetrabutylammonium bromide (0.2 mmol) and Tert-butyl N—[N-[(2-methylpropan-2-yl)oxycarbonyl]carbamimidoyl]carbamate (1 mmol, Sigma-Aldrich catalogue id: 496871) were added. After few minutes, a solution of (E)-1-bromobut-2-ene (2.4 mmol, Sigma-Aldrich catalogue ID: C86405) in $CH_2Cl_2/CH_3CN$ (19:1, 3.5 mL) was added dropwise and the resulting solution was stirred at r.t. for 16-18 h. The reaction mixture was then poured on ice and the aqueous layer was extracted with $CH_2Cl_2$ (2×5 mL). The combined organic phases were washed with brine, dried over $Na_2SO_4$, filtered and concentrated under reduced pressure. The crude products were purified by flash column Chromatography ($SiO_2$) using 1:9 $MeOH/CH_2Cl_2$ as the eluent to yield the title compound tert-butyl N-but-2-enyl-N—[N'-[(2-methylpropan-2-yl)oxycarbonyl]-N-methylsulfanylcarbamimidoyl]carbamate.

Time 16 h, yield 70%. $^1H$ NMR (400 MHz, $CDCl_3$) δ 5.34-5.21 (2H, m), 3.69-3.68 (2H, d, J=8 Hz), 2.02-2.01 (3H, s), 1.15 (9H, s), 1.12 (9H, m) ppm.
$^{13}C$ NMR ($CDCl_3$) δ 162.8, 157.7, 151.5, 129.6, 126.5, 82.0, 82.4, 45.4, 27.9, 17.5, 15.3 ppm.
LCMS m/z (ES+) m/z=710.9 $[2M+Na]^+$, 367.0 $[M+Na]^+$, 345.1 $[M+H]^+$
Elemental analysis for $C_{16}H_{28}N_2O_4S$: Calcd. C, 55.79; H, 8.19; N, 8.13. Found C, 55.83; H, 8.21; N, 8.34.

Procedure for the Preparation of tert-butyl N—[N-[(E)-but-2-enyl]-N'-[(2-methylpropan-2-yl)oxycarbonyl]carbamimidoyl]-N-[8-[4-[(2-methylpropan-2-yl)oxycarbonylimino]-6-oxo-12-oxa-3,5,7-triazabicyclo[11.4.0]heptadeca-1 (13), 14,16-trien-7-yl]octyl]carbamate 15

15

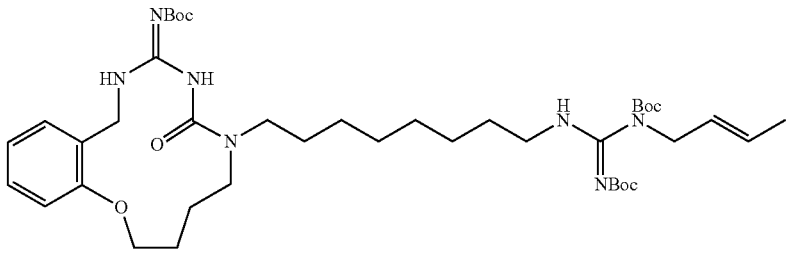

To a stirred solution of the compound 14 (0.097 mmol) in dry THF (5 ml) a solution of tert-butyl N-but-2-enyl-N—[N'-[(2-methylpropan-2-yl)oxycarbonyl]-N-methylsulfanyl carbamimidoyl]carbamate (0.10 mmol) in dry THF (4 ml) was added dropwise. Then $Et_3N$ (0.14 mmol) was added. The mixture was then stirred at reflux overnight. The solvent was evaporated under reduced pressure, and the residue was purified by flash chromatography ($SiO_2$) using 1:1 hexane-$Et_2O$ as the eluent affording title compound 15.
Yield 50%. $^1H$ NMR (400 MHz, $CDCl_3$) δ 11.97 (1H, s), 8.44 (1H, s), 7.28-6.74 (4H, m), 5.57-5.55 (1H, m), 5.44-5.41 (1H, m), 4.09-4.07 (2H, d, J=8 Hz), 4.02-4.00 (2H, d, J=6.4 Hz), 3.31-3.30 (2H, m), 3.17-3.10 (6H, m), 1.60-1.58 (3H, d, J=6.4 Hz), 1.42-1.36 (27H, m), 1.22-1.17 (16H, m) ppm.
$^{13}C$ NMR ($CDCl_3$) δ 163.9, 158.0, 155.5, 153.4, 153.0, 130.3, 128.3, 128.2, 127.9, 126.1, 120.4, 111.7, 81.9, 67.1, 47.4, 46.3, 43.7, 37.1, 39.5, 29.3, 28.5, 28.0, 26.9, 26.7, 24.5, 23.8, 20.9, 17.6 ppm.
LCMS m/z (ES+) m/z=808.3$[M+Na]^+$, 824.0 $[M+K]^+$, 786.2$[M+H]^+$.
Elemental analysis for $C_{41}H_{67}N_7O_8$: Calcd. C, 62.65; H, 8.59; N, 12.47. Found C, 63.08; H, 8.98; N, 12.84.

Procedure for the Preparation of Example 16:
1-[(E)-but-2-enyl]-3-[8-(4-imino-6-oxo-12-oxa-3,5,7-triazabicyclo[11.4.0]heptadeca-1(13),14,16-trien-7-yl)octyl]guanidine 16

16

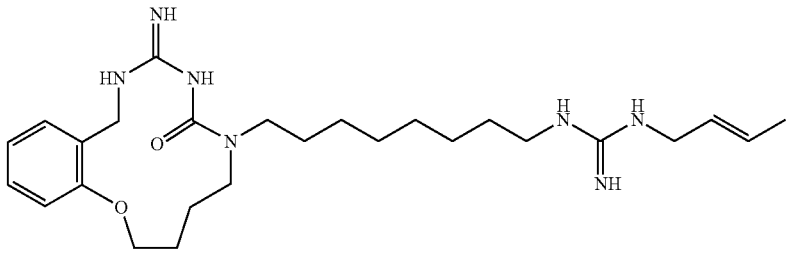

Guanylated compound 15 (0.025 mmol) was dissolved in dry DCM (30 mL for 1 mmol) and treated with a 10% solution of freshly distilled TFA. The resulting solution was stirred at room temperature under argon. After 24 h the reaction mixtures were concentrated under reduced pressure affording the crude title compound 16 (brown oil) in quantitative yield.

Yield quantitative. $^1$H NMR (400 MHz, MeOD) δ 7.33-6.94 (4H, m), 5.68-5.64 (1H, m), 5.44-5.41 (1H, m), 4.44-4.38 (2H, m), 4.21-4.20 (2H, m), 3.68-3.67 (2H, d, J=4.8 Hz), 3.54 (2H, m), 3.30-3.28 (2H, m), 3.12-3.09 (2H, t, J=6.8 Hz), 1.65-1.64 (3H, m), 1.55-1.45 (4H, m), 1.32-1.21 (12H, m) ppm.

$^{13}$C NMR (MeOD) δ 163.5, 157.6, 156.2, 155.8, 131.0, 129.9, 128.6, 127.9, 127.1, 124.8, 121.3, 111.4, 69.0, 47.2, 43.0, 41.0, 31.5, 29.2, 28.7, 28.4, 27.2, 26.1, 24.9, 22.0, 16.2 ppm.

LCMS m/z (ES+) m/z=508.3[M+Na]$^+$, 524.0 [M+K]$^+$, 486.2[M+H]$^+$.

Elemental analysis for $C_{26}H_{43}N_7O_2$: Calcd. C, 64.30; H, 8.92; N, 20.19. Found C, 64.68; H, 9.08; N, 20.84.

Example 17

1-[(E)-but-2-enyl]-3-[8-(4-imino-6-oxo-13-oxa-3,5,7-triazabicyclo[12.4.0]octadeca-1(14),15,17-trien-7-yl)octyl]guanidine 17

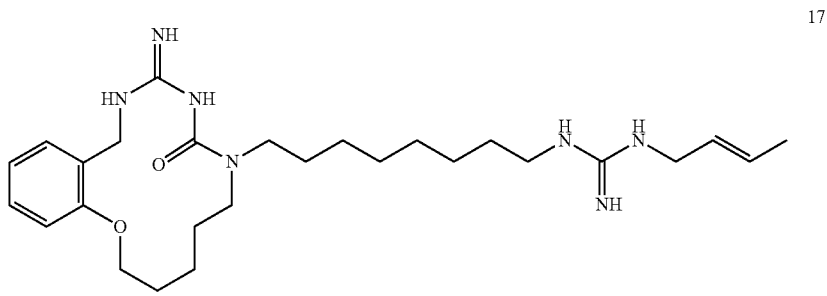 [SMILES: C/C=C/CNC(=N)NCCCCCCCCN1CCCCCOc2ccccc2CNC(=N)NC1=O]

17

Compound 17 was synthesized starting from the appropriate intermediate 1f, according to the procedure as for example 16.

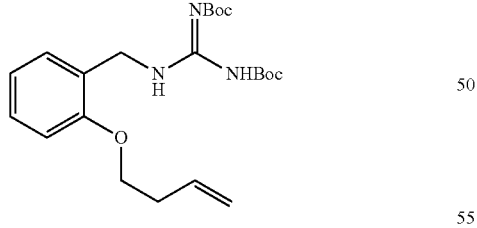

1f

Analytical Data for Compound 17

$^1$H NMR (400 MHz MeOD) δ 7.23-6.88 (4H, m), 5.62-5.64 (1H, m), 5.40-5.35 (1H, m), 4.43-4.42 (2H, m), 4.06 (2H, m), 3.65 (2H, m), 3.45-3.41 (2H, m), 3.23 (2H, m), 3.08-3.00 (2H, m), 1.63-1.62 (3H, m), 1.49-1.48 (6H, m), 1.28-1.17 (12H, m) ppm.

$^{13}$C NMR (100 MHz MeOD) δ 163.5, 156.7, 156.2, 154.7, 130.0, 128.5, 127.9, 127.1, 124.8, 120.0, 111.1, 64.6, 49.2, 46.6, 42.4, 41.0, 39.6, 28.7, 28.3, 27.0, 26.0 ppm.
LC-MS m/z (ES+) m/z=522.3[M+Na]$^+$, 538.0 [M+K]$^+$, 500.2[M+H]$^+$

Example 18

1-[(E)-but-2-enyl]-3-[8-(4-imino-6-oxo-14-oxa-3,5,7-triazabicyclo[13.4.0]nonadeca-1(15), 16,18-trien-7-yl)octyl]guanidine 18

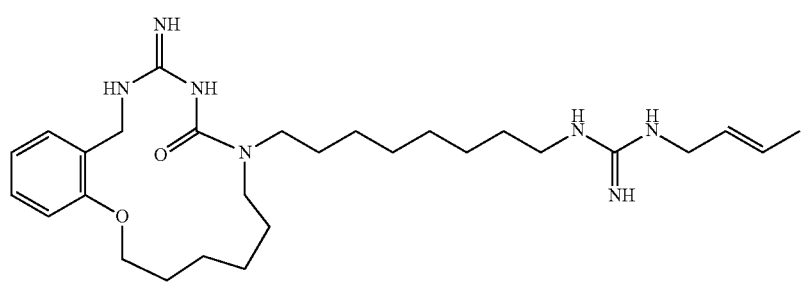

Compound 18 was synthesized starting from the appropriate intermediate 1g, according to the procedure as for example 16.

1g

Analytical Data for Compound 18

$^1$H NMR (400 MHz MeOD) δ 12.31 (1H, s), 8.05 (1H, s), 7.26-7.22 (2H, m), 6.92-6.84 (2H, m), 5.66-5.65 (1H, m), 5.49-5.42 (1H, m), 4.37 (2H, m), 3.97 (2H, m), 3.68 (2H, m), 3.51 (2H, m), 3.30 (2H, m), 3.15-3.11 (4H, m), 1.63-1.62 (3H, m), 1.50-1.48 (6H, m), 1.28-1.23 (12H, m) ppm.

$^{13}$C NMR (100 MHz MeOD) δ 163.7, 157.5, 156.1, 155.8, 130.3, 128.5, 124.9, 119.8, 110.9, 67.2, 53.3, 46. 42.5, 41.0, 29.0, 28.7, 28.4, 27.1, 26.7, 26.4, 26.4, 26.3, 26.2, 26.1, 26.0 ppm.

LC-MS m/z (ES+) m/z=536.3[M+Na]$^+$, 552.0 [M+K]$^+$, 514.2[M+H]$^+$

Example 19

1-[(E)-but-2-enyl]-3-[8-(6-imino-2,8-dioxo-1-oxa-5,7,9-triazacyclotetradec-9-yl)octyl]guanidine 19

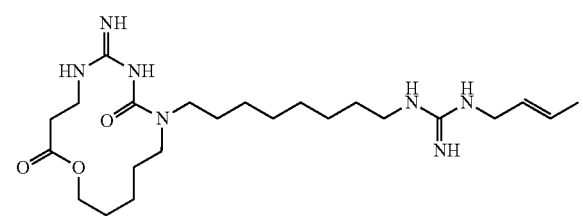

Compound 19 was synthesized according to scheme 1 by reacting intermediate 1b with intermediate 3a, and applying a similar procedure as for example 16.

The synthesis of intermediate 1 b is described in scheme 3.

Scheme 3

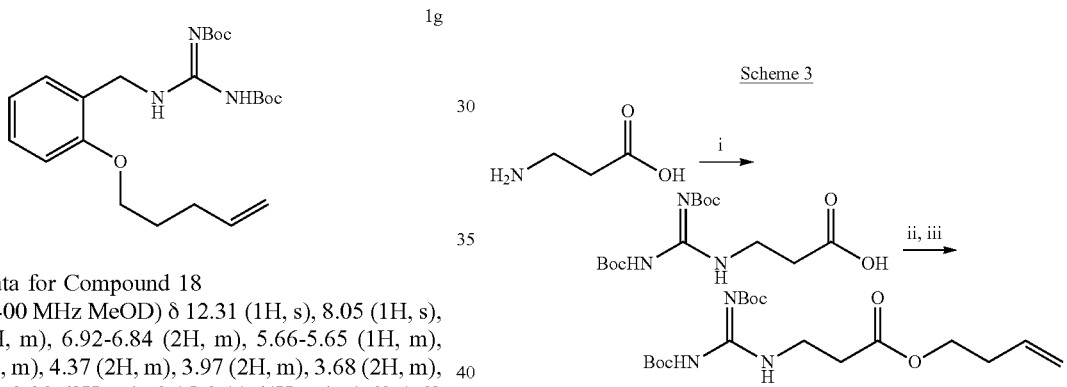

Reagents and conditions: (i) (BocNH)$_2$C=NTf, Et$_3$N, DCM, (ii) TMSCI, Et$_3$N, DCM, reflux; (iii) DMAP, DCC, but-3-en-1-ol (sigma-Aldrich, catalogue ID: 496839), DCM, rt 24 h;

3-aminopropanoic acid (600 mg 6.74 mmol, Sigma-Aldrich catalogue ID: 146064) was dissolved in CH$_2$Cl$_2$ (10 ml) and trimethylsilyl chloride (0.86 ml, 6.74 mmol) was added dropwise at room temperature over 5 min. The reaction mixture was then refluxed for 1 h and then cooled to 0° C. Triethylamine (1.22 ml, 8.76 mmol) was then added followed by N,N'-bis(tert-butoxycarbonyl)-S-methylisothiourea (977 mg, 3.37 mmol). The resulting mixture was refluxed for 1 h, then cooled down to room temperature and added with MeOH (10 ml) and stirred for 10 min. Solvent was then evaporated and the residue diluted with water and then acidified with HCl 1N to pH 2. The mixture was extracted with AcOEt (2×10 ml). The organic layers were collected and washed with brine, dried over anhydrous Na$_2$SO$_4$ and evaporated under reduce pressure. The residue was used in the next step without any further purification. To a solution of 3-[[N,N'-bis[(2-methylpropan-2-yl)oxycarbonyl]carbamimidoyl]amino]propanoic acid (8.98 mmol) in dry DCM (20 ml), the but-3-en-1-ol (17.96 mmol, Sigma-Aldrich catalogue ID: 496839) and DMAP (0.89 mmol)

were added. The mixture was cooled down to 0° C. and DCC (13.47 mmol) was then added. The mixture was allowed to warm to r.t. overnight while stirring under argon. The white precipitated formed during the reaction was filtered off. The solution was then washed with brine, dried over $Na_2SO_4$ and concentrated in vacuum. The residue was purified by flash chromatography using hexane $Et_2O$ 4:6 as eluent affording desired compound 1b, but-3-enyl 3-[[N,N-bis[(2-methylpropan-2-yl)oxycarbonyl]carbamimidoyl]amino]propanoate.

Analytical Data for Compound 19

$^1$H NMR (400 MHz MeOD) δ 12.31 (1H, s), 8.05 (1H, s), 5.64 (1H, m), 5.42 (1H, m), 4.13 (2H, m), 3.78 (2H, m), 3.64 (2H, m), 3.43 (2H, m), 3.08 (2H, m), 2.51 (2H, m), 1.63 (3H, m), 1.55 (4H, m), 1.49 (4H, m), 1.27 (12H, m) ppm.

$^{13}$C NMR (100 MHz MeOD) δ 171.3, 171.1, 155.1, 154.0, 137.5, 128.6, 63.9, 42.5, 41.0, 37.6, 34.1, 29.2, 28.7, 28.4, 27.6, 26.1, 21.9, 18.7 ppm.

LCMS m/z (ES+) m/z=488.0[M+Na]$^+$, 466.2[M+H]$^+$.

Example 20

1-[(E)-but-2-enyl]-3-[8-(6-imino-2,8-dioxo-1-oxa-5,7,9-triazacyclopentadec-9-yl)octyl]guanidine 20

3-aminopropanoic acid (600 mg 6.74 mmol, Sigma-Aldrich catalogue ID: 146064) was dissolved in $CH_2Cl_2$ (10 ml) and trimethylsilyl chloride (0.86 ml, 6.74 mmol) was added dropwise at room temperature over 5 min. The reaction mixture was then refluxed for 1 h and then cooled to 0° C. Triethylamine (1.22 ml, 8.76 mmol) was then added followed by N,N'-bis(tert-butoxycarbonyl)-S-methylisothiourea (977 mg, 3.37 mmol). The resulting mixture was refluxed for 1 h, then cooled down to room temperature and added with MeOH (10 ml) and stirred for 10 min. Solvent was then evaporated and the residue diluted with water and then acidified with HCl 1N to pH 2. The mixture was extracted with AcOEt (2×10 ml). The organic layers were collected and washed with brine, dried over anhydrous $Na_2SO_4$ and evaporated under reduce pressure. The residue was used in the next step without any further purification. To a solution of 3-[[N,N'-bis[(2-methylpropan-2-yl)oxycarbonyl]carbamimidoyl]amino]propanoic produced in the previous step (8.98 mmol) in dry DCM (20 ml), the pent-4-en-

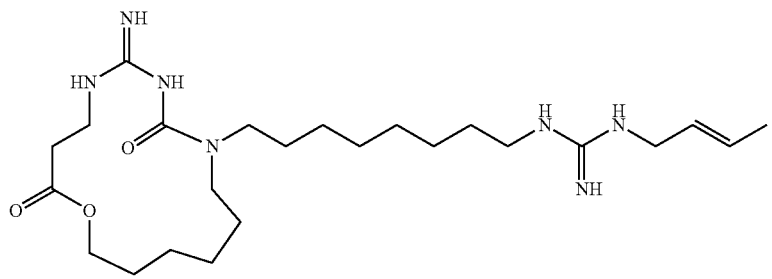

20

Compound 20 was synthesized according to scheme 1 by reacting intermediate 1h with intermediate 3a, and applying a similar procedure as described for example 16.

The synthesis of intermediate 1h is described in scheme 4

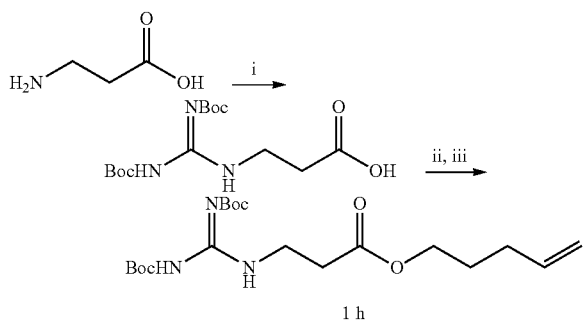

Scheme 4

Reagents and conditions: (i) (BocNH)$_2$C=NTf, Et$_3$N, DCM (ii) TMSCI, Et$_3$N, DCM, reflux; (iii) DMAP, DCC, pent-4-en-1-ol (sigma-Aldrich, catalogue ID: 111279), DCM, rt 24 h;

1-ol (17.96 mmol, Sigma-Aldrich catalogue ID: 111279) and DMAP (0.89 mmol) were added. The mixture was cooled down to 0° C. and DCC (13.47 mmol) was then added. The mixture was allowed to warm to r.t. overnight while stirring under argon. The white precipitated formed during the reaction was filtered off. The solution was then washed with brine, dried over $Na_2SO_4$ and concentrated in vacuum. The residue was purified by flash chromatography using hexane-$Et_2O$ 4:6 as eluent affording desired compound 1b, but-3-enyl 3-[[N,N'-bis[(2-methylpropan-2-yl)oxycarbonyl]carbamimidoyl]amino]propanoate.

Analytical Data for Compound 20

$^1$H NMR (300 MHz MeOD) δ 12.31 (1H, s), 8.05 (1H, s), 5.65 (1H, m), 5.43 (1H, m), 4.06 (2H, m), 3.68 (2H, m), 3.58 (2H, m), 3.44 (2H, m), 3.30 (2H, m), 3.11-3.07 (2H, m), 2.62-2.59 (2H, m), 1.63 (3H, d, J=6.0 Hz), 1.51 (8H, m), 1.27 (12H, m) ppm.

$^{13}$C NMR (100 MHz MeOD) δ 171.3, 171.1, 155.1, 154.0, 136.1, 129.2, 76.4, 41.1, 41.0, 37.3, 36.8, 29.4, 29.2, 29.3, 29.0, 28.8, 28.4, 28.5, 26.1, 21.8, 19.0 ppm.

LCMS m/z (ES+) m/z=502.0[M+Na]$^+$, 480.2[M+H]$^+$.

Example 21
1-[(E)-but-2-enyl]-3-[6-[4-imino-6-oxo-2-(1-phenyl-triazol-4-yl)-14-oxa-3,5,7-triazabicyclo[13.4.0]nonadeca-1(15),16,18-trien-7-yl]hexyl]guanidine 21
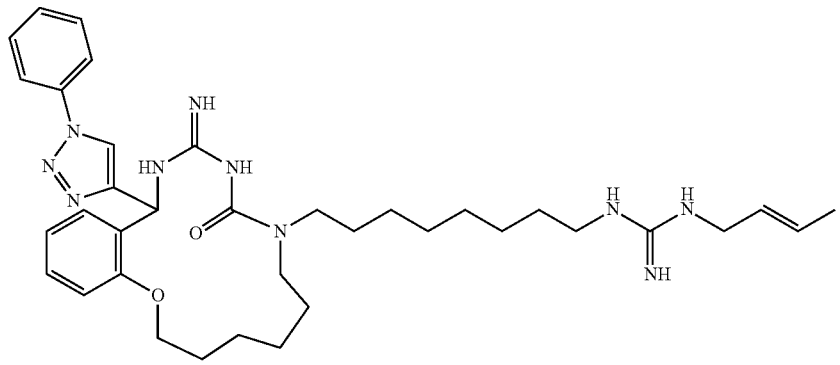
Compound 21 was synthesized according to scheme 1 by reacting intermediate 1c with intermediate 3a and applying a similar procedure as described for example 16.
The synthesis of intermediate 1c is described in scheme 5.
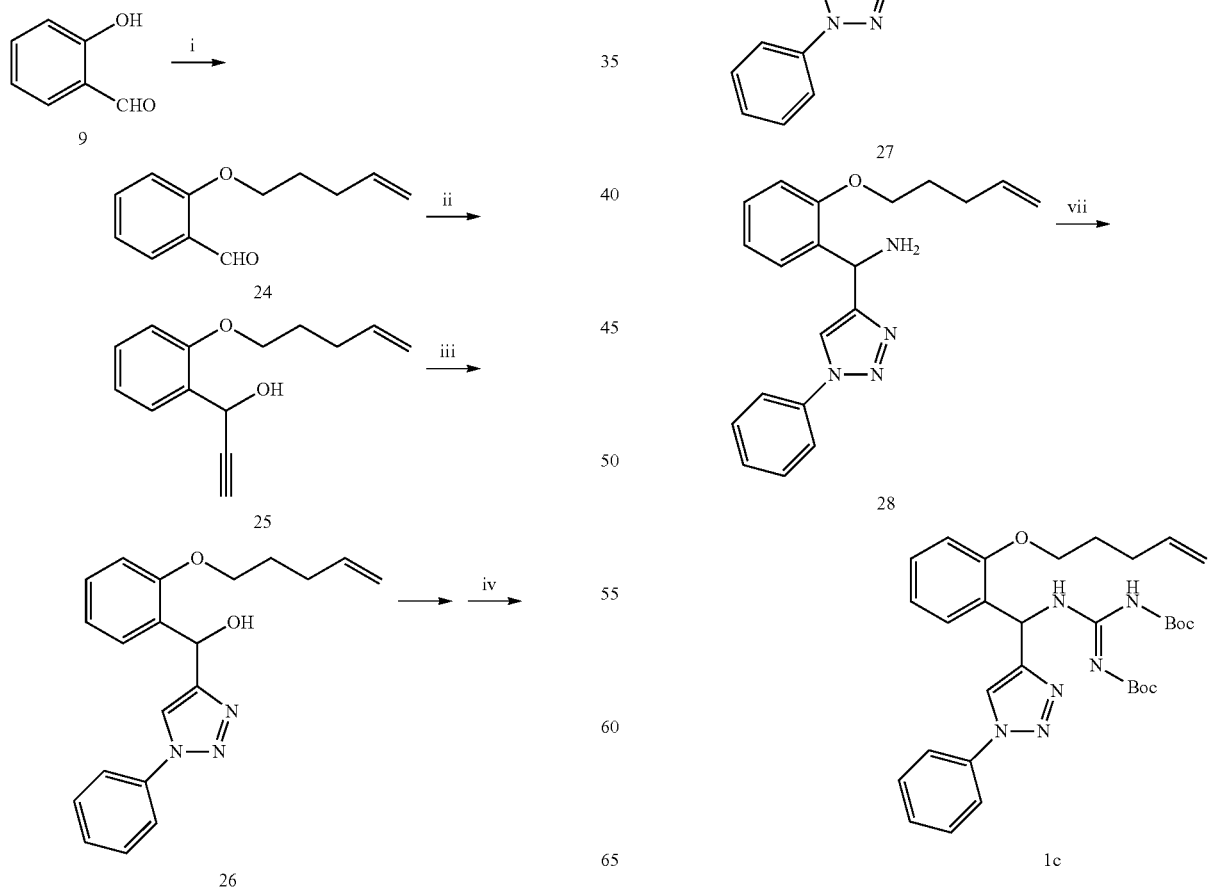

Reagents and Conditions:
(i) Br(CH$_2$)$_3$CH=CH$_2$ (1.2 eq), K$_2$CO$_3$ (1.2 eq), CH$_3$CN, reflux, 12 h (ii) Ethinylmagnesium bromide (1.5 eq), THF, −15° C., 4 h (iii) N$_3$Ph (2.5 eq), NaAscorbate (0.1 eq), CuSO$_4$ (0.01 eq), H$_2$O/t-BuOH, MW, 125° C., 30' (iv) MnO$_2$ (10 eq), DCM, r.t. 18 h (v) NH$_2$OH (2.5 eq), Py (1.2), EtOH, reflux, 4 h (vi) Zn (10.0 eq), HCl (2N, 10.0 eq), THF, reflux, 2 h (vii) (BocNH$_2$)$_2$C=Tf (1.1 eq), Et$_3$N (2.0), DCM, r.t. 18 h Analytical Data of Compound 21

$^1$H NMR (400 MHz, MeOD) δ 8.56 (1H bs), 7.87-7.85 (2H, d, J=7.2 Hz), 7.59-7.55 (2H, t, J=8.0 Hz), 7.50-7.47 (1H, t, J=7.2 Hz), 7.39-7.35 (1H, t, J=7.2 Hz), 7.30-7.29 (1H, d, J=4.0 Hz), 7.07-7.05 (1H, t, J=8.4 Hz), 6.90 (2H, bs), 6.35 (1H, s), 5.73-5.67 (1H, m), 5.47-5.43 (1H, m), 4.13 (2H, s), 3.71-3.70 (2H, d, J=5.6 Hz), 3.47 (2H, s), 3.33 (2H, s), 3.07-3.04 (2H, t, J=6.8), 1.69-1.67 (3H, d, J=6.0 Hz), 1.59-1.52 (8H, m), 1.28-1.23 (12H, m)

$^{13}$C NMR (400 MHz, MeOD) δ 163.6, 162.4, 156.3, 156.1, 153.1, 152.1, 149.0, 137.5, 137.0, 131.5, 131.2, 130.4, 129.5, 128.8, 127.6, 124.9, 120.5, 120.15, 119.4, 119.2, 115.3, 97.01, 67.6, 66.4, 50.4, 48.9, 48.3, 47.5, 45.5, 42.5, 41.0, 30.7, 30.1, 29.2, 28.8, 28.4, 26.1, 17.5

LCMS m/z (ES+) m/z=329.1 [M+2H]$^{2+}$, 657.3 [M+H]$^+$, 695.3 [M+Na]$^+$

Example 22

1-[(2E)-but-2-en-1-yl]-3-(8-{16-imino-14-oxo-2-oxa-13,15,17-triazatricyclo[17.4.0.0$^{4,9}$]tricosa-1(19),4(9),5,7,20,22-hexaen-13-yl}octyl)guanidine 22

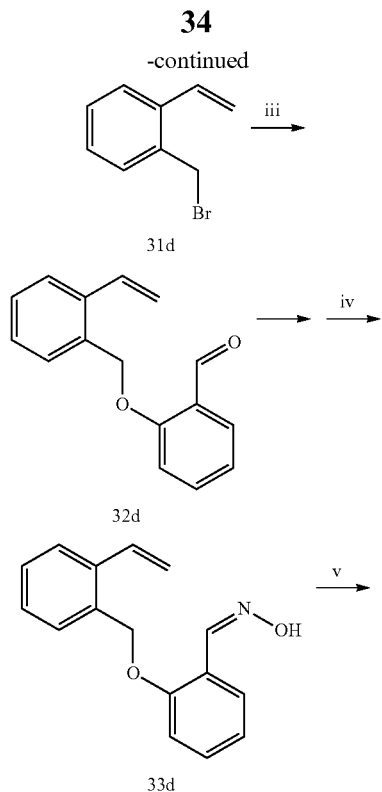

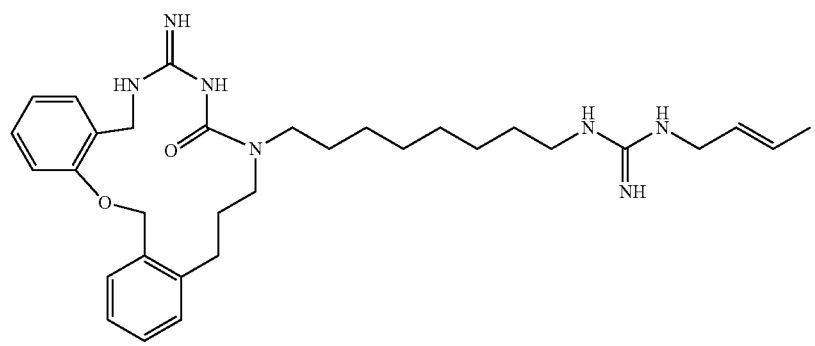

Compound 22 was synthesized according to according to scheme 1 by reacting intermediate 1d with intermediate 3a and applying a similar procedure as for example 16.

The synthesis of intermediate is 1d reported in scheme 6.

Scheme 6

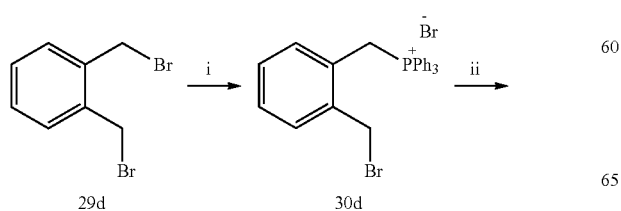

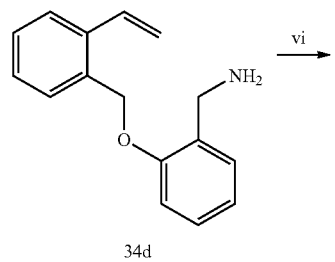

-continued

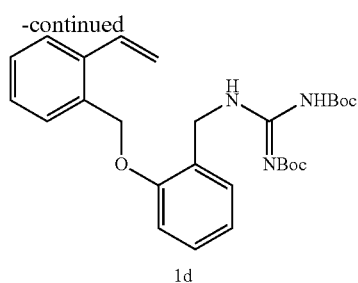

1d

Reagents and Conditions:
(i) PPh$_3$ (1.1 eq), THF, reflux, 12 h (ii) CH$_2$O (1.8 eq), KOH (2.0 eq), DCM, r.t., 1 h (iii) Salicylaldehyde (1.0 eq), K$_2$CO$_3$ (1.5 eq), CH$_3$CN, reflux, 12 h (iv) NH$_2$OH (2.5 eq), Py (1.2 eq), EtOH, reflux, 4 h (v) Zn (10.0 eq), HCl (2N, 10 eq), THF, reflux, 2 h (iv) (BocNH$_2$)$_2$C=Tf (1.1 eq), Et$_3$N (2.0 eq), DCM, r.t. 18 h.

Analytical Data of Compound 22.

$^1$H NMR (400 MHz, MeOD) δ 7.46-7.44 (1H, d, J=6.0 Hz), 7.35 (2H, m), 7.23 (3H, m) 6.98 (1H, m), 6.87-6.88 (1H, t, J=4.5), 6.84 (1H, m), 5.75-5.69 (1H, m), 5.51-5.48 (1H, m), 5.07 (2H, s), 4.46-4.40 (2H, d, J=24 Hz), 3.74-3.72 (2H, d, J=5.6 Hz), 3.40-3.30 (4H, m), 3.17-3.13 (2H, t, J=8.8), 2.63-2.59 (2H, t, J=7.4), 1.72-1.69 (3H, d, J=6.0 Hz), 1.57-1.54 (4H, m), 1.32-1.28 (10H, m)

$^{13}$C NMR (400 MHz, MeOD) δ 163.7, 156.4, 155.9, 153.2, 136.8, 136.6, 135.3, 134.7, 133.7, 129.7, 129.6, 129.4, 128.6, 128.1, 125.7, 125.6, 124.9, 121.1, 119.5, 114.8, 111.9, 76.2, 48.4, 47.5, 42.5, 41.0, 40.4, 37.4, 29.2, 28.9, 28.8, 28.7, 28.5, 28.4, 28.1, 26.1, 16.3

LCMS m/z (ES+) m/z=281.7 [M+2H]$^{2+}$, 562.3 [M+H]$^+$.

Example 23

1-[(2E)-but-2-en-1-yl]-3-(8-{12-imino-14-oxo-3-oxa-11,13,15-triazatricyclo[17.3.1.0$^{4,9}$]tricosa-1(23),4(9),5,7,19,21-hexaen-15-yl}octyl)guanidine Compound 23 was synthesized according to according to scheme 1 by reacting intermediate 1e with intermediate 3a and applying a similar procedure as for example 16.

The synthesis of intermediate 1e reported in scheme 7.

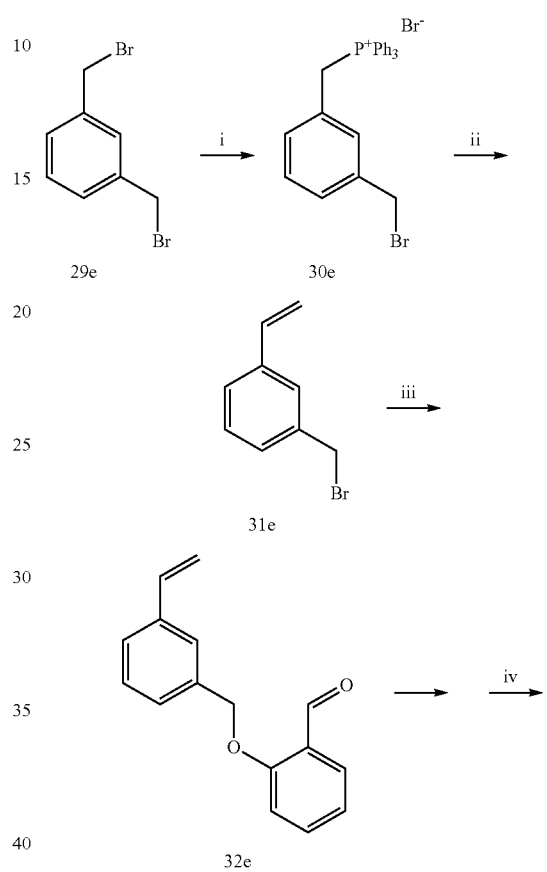

Scheme 7

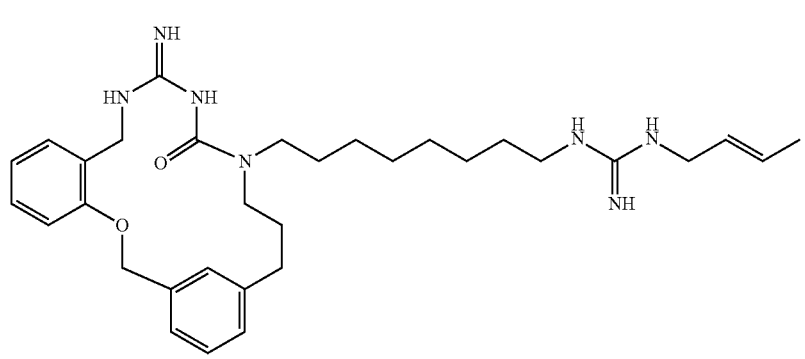

23

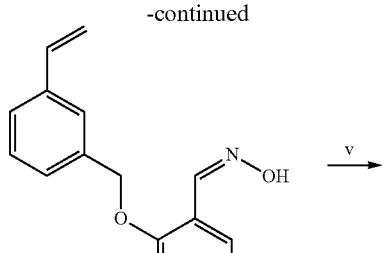

Reagents and Conditions:

(i) PPh₃ (1.1 eq), THF, reflux, 12 h (ii) CH₂O (1.8 eq), KOH (2.0 eq), DCM, r.t., 1 h (iii) Salicylaldehyde (1.0 eq), K₂CO₃ (1.5 eq), CH₃CN, reflux, 12 h (iv) NH₂OH (2.5 eq), Py (1.2 eq), EtOH, reflux, 4 h (v) Zn (10.0 eq), HCl (2N, 10 eq), THF, reflux, 2 h (iv) (BocNH₂)₂C=Tf (1.1 eq), Et₃N (2.0 eq), DCM, r.t. 18 h.

Analytical Data of Compound 23

$^1$H NMR (400 MHz, MeOD) δ 7.31-7.19 (7H, m), 7.07 (1H, s), 6.97-6.93 (1H, t, J=7.2), 5.75-5.70 (1H, m), 5.59-5.47 (1H, m), 5.13 (2H, s), 4.53 (2H, s), 3.74-3.72 (2H, d, J=4.8 Hz), 3.35 (2H, s), 3.17-3.13 (4H, t, J=7.2), 2.66-2.65 (2H, d, J=5.2), 2.09 (2H, s), 1.71-1.69 (3H, d, J=6.4 Hz), 1.56-1.48 (4H, m), 1.27-1.19 (10H, m)

$^{13}$C NMR (400 MHz, MeOD) δ 161.7, 157.2, 155.9, 154.1, 153.2, 147.8, 141.1, 136.6, 130.1, 130.0, 128.8, 128.2, 127.9, 127.4, 125.9, 125.4, 124.8, 122.7, 120.2, 111.4, 70.2, 69.2, 44.8, 44.4, 42.6, 42.5, 41.0, 37.4, 31.5, 29.2, 28.8, 28.7, 28.5, 27.5, 27.1, 26.1, 25.8, 16.3

LCMS m/z (ES+) m/z=281.7 [M+2H]$^{2+}$, 562.3 [M+H]$^+$

Biological Assays

Antimicrobial Susceptibility Testing

Sterile plastic microtitration plates containing flat-bottomed wells were used. The plates contained serial dilution of the antifungal agents with a volume of assay medium of 100 μL/well. Two drug-free medium wells were used as sterility and growth controls. The trays were inoculated with 100 μL/well of the final inoculum, with the exception of sterility control wells. The range of concentrations tested for each drug was 1.25-80 μM. The microtitration plates were incubated at 37° C. for 24 h. The minimal inhibitory concentrations (MICs) were determined at 24 h both visually and spectrophotometrically measuring the turbidity at 595 nm with a Varian model 1475 spectrophotometer.

The various strain tested are indicated in Table 1.

TABLE 1

| Species | Strains | Source |
|---|---|---|
| Candida Albicans | ATCC60193, ATCC14053, ATCC90028, ATCC24433, ATCC200955, ATCC10231, ATCC76615, ATCC2091, ATCC96110, ATCC36232, ATCC90255, ATCC44806, ATCC44373, ATCC90257, ATCC44808, ATCC56883, ATCC48274, ATCC34133, ATCC90268, ATCC52302, ATCC38289, ATCC56880 | ATCC (LGC Standards) |
| Candida guilliermondii | ATCC56822, ATCC22017, ATCC34134, ATCC22949, ATCC76759, ATCC20118, ATCC20382, ATCC6260, ATCC22948, ATCC42050 | ATCC (LGC Standards) |
| Candida krusei | ATCC32545, ATCC2340, ATCC34077, ATCC38293, ATCC32672, ATCC32672, ATCC14243, ATCC201071, ATCC22985, ATCC20405, ATCC90878, ATCC2159, ATCC34135 | ATCC (LGC Standards) |
| Candida parapsilosis | ATCC-MYA-4646, ATCC28476, ATCC22019, ATCC58789, ATCC20246, ATCC96140, ATCC20181, ATCC16632, ATCC20224, ATCC7333, ATCC90018, ATCC20179, ATCC96137, ATCC7330, ATCC96142, ATCC201075, ATCC201076, ATCC58791, ATCC34136, ATCC20406, ATCC96041, ATCC90875, ATCC60548 | ATCC (LGC Standards) |
| Candida tropicalis | ATCC15114, ATCC38292, ATCC28776, ATCC28724, ATCC20005, ATCC22577, ATCC60557, ATCC46536, ATCC42678, ATCC36729, ATCC201380 | ATCC (LGC Standards) |

TABLE 1-continued

Strains used in the biological assay.

| Species | Strains | Source |
| --- | --- | --- |
| Candida kefyr | ATCC8618, ATCC66028D, ATCC8641, ATCC204093, ATCC44691, ATCC9767, ATCC2540, ATCC8654, ATCC8619, ATCC200553 | ATCC (LGC Standards) |
| Candida glabrata | ATCC15545, ATCC15126, ATCC90876, ATCC32554, ATCC66032, ATCC90525, ATCC60406, ATCC64677, ATCC36909D, ATCC2001, ATCC200989, ATCC46433, ATCC58561, ATCC26512, ATCC32936, ATCC48435, ATCC200918, ATCC28226, ATCC28290, ATCC38326, ATCC90030, ATCC34139, ATCC32312, ATCC201069, ATCC MYA-275, ATCC MYA2950D-5 | ATCC (LGC Standards) |

Results

Results of biological tests are shown in Table 2, biological data are reported as $MIC_{90}$ that is the minimum concentration required to inhibit the growth of at least the 90% of the strains tested for each species.

TABLE 2

Antifungal activity of examples 16-23

| Species (No. strains tested) | $MIC_{90}$ (μg/mL)[a] | | | | | | | | |
| --- | --- | --- | --- | --- | --- | --- | --- | --- | --- |
| | F[b] | 16 | 17 | 18 | 19 | 20 | 21 | 22 | 23 |
| C. albicans (22) | 2 | 16 | 4 | 4 | 32 | 16 | 32 | 64 | 256 |
| C. guilliermondii (10) | 4 | 16 | 2 | 2 | 32 | 8 | 32 | 64 | 256 |
| C. krusei (13) | 256 | 32 | 8 | 4 | 64 | 32 | 128 | 256 | 256 |
| C. parapsilosis (24) | 0.5 | 8 | 2 | 2 | 32 | 8 | 32 | 64 | 256 |
| C. tropicalis (11) | 2 | 8 | 2 | 1 | 32 | 16 | 64 | 128 | 256 |
| C. kefyr (10) | 1 | 4 | 4 | 2 | 32 | 16 | 64 | 128 | 256 |
| C. glabrata (26) | 16 | 64 | 8 | 16 | 64 | 32 | 64 | 128 | 128 |

[a]$MIC_{90}$ values were determined at 24 h both visually and spectrophotometrically.
[b]Fluconazole Compounds 16, 17 and 18 possessing an aromatic ring fused to the macrocyclic core proved to be more active when compared to compounds 19 and 20 bearing an ester moiety. It is noteworthy that compounds 18 and 20, with a macrocyclic core of 15 atoms showed one of the highest activity toward C. albicans, C. guillermondii and C. parapsilosis when compared with homologue compounds with a lover number of atoms in the macrocyclic core. In particular compounds 18 and 20 are more active than fluconazole on C. guillermondii and C. krusei.

Mutant Strains

Compounds 16-19 were thus assayed against mutant C. albicans and C. glabrata strains bearing mutation on ERG11, CDR1, CDR2, SNQ2 and MDR1 genes, these mutants were obtained from clinical isolates and have been reported in the scientific literature. The ERG11 gene, which encodes the cytochrome P450, confers resistance to drugs belonging to the azole class, such as voriconazole and fluconazole. CDR1 and CDR2 genes encodes for ATP binding cassette (ABC) transporters, their overexpression confers resistance to the azole class. MDR1 gene, which encodes a membrane transport protein of the major facilitator superfamily, confers resistance to a broad range of drugs and toxic compounds. The SNQ2 gene encodes for yet another ABC transporter that confers resistance to azole and non-azole drugs.

Voriconazole, an azole active on fluconazole resistant strains, was chosen as reference compound. Data are reported in Table 3 as MIC value (minimum inhibitory concentration (MIC) is the lowest concentration of an agent that will inhibit the visible growth of a microorganism after overnight incubation) obtained as the mean of three measurements for each strain.

TABLE 3

Antifungal activity of compounds 16-19 on C. albicans and C. glabrata fluconazole resistant strains.

| Strains | Species | Resistance mechanism | MIC (μg/mL)[a] | | | | | |
| --- | --- | --- | --- | --- | --- | --- | --- | --- |
| | | | FLU[b] | VOR[c] | 16 | 17 | 18 | 19 |
| DSY284 | C. albicans | ERG11 Mutation | 256 | 4 | 16 | 2 | 8 | 16 |
| DSY296 | C. albicans | ERG11 Mutation | 128 | 8 | 16 | 4 | 16 | 16 |
| DSY348 | C. albicans | ERG11 Mutation | 32 | 0.25 | 8 | 2 | 8 | 8 |
| DSY289 | C. albicans | ERG11 Mutation (2) | 256 | 8 | 8 | 2 | 8 | 8 |
| DSY291 | C. albicans | ERG11 Mutation (2) | 2 | 0.03 | 8 | 4 | 16 | 8 |
| DSY292 | C. albicans | ERG11 Mutation (3) | 64 | 2 | 16 | 4 | 16 | 16 |
| DSY775 | C. albicans | ERG11 Mutation | 128 | 8 | 16 | 4 | 16 | 16 |
| DSY732 | C. albicans | ↑CDR1-CDR2 | 16 | 0.25 | 8 | 2 | 16 | 8 |
| DSY735 | C. albicans | ↑CDR1-CDR2 | 64 | 2 | 8 | 2 | 16 | 8 |
| DSY750 | C. albicans | ↑MDR1 | 2 | 0.016 | 16 | 4 | 16 | 16 |
| DSY751 | C. albicans | ↑MDR1, ERG11 Mutation | 256 | 0.25 | 16 | 4 | 16 | 16 |
| DSY2323 | C. albicans | ↑CDR2-MDR1 | 32 | 0.25 | 8 | 4 | 16 | 16 |
| DSY530 | C. glabrata | ↑CDR1 | 64 | 0.5 | 64 | 8 | 32 | 64 |
| DSY754 | C. glabrata | ↑CDR1 | 64 | 2 | 64 | 16 | 32 | 64 |
| DSY756 | C. glabrata | ↑CDR1-CDR2-SNQ2 | 128 | 4 | 64 | 8 | 64 | 128 |

TABLE 3-continued

Antifungal activity of compounds 16-19 on *C. albicans* and *C. glabrata* fluconazole resistant strains.

| Strains | Species | Resistance mechanism | FLU[b] | VOR[c] | 16 | 17 | 18 | 19 |
|---------|---------|----------------------|--------|--------|----|----|----|----|
| DSY2254 | C. glabrata | ↑CDR1-CDR2 | 128 | 2 | 64 | 16 | 64 | 128 |
| DSY2271 | C. glabrata | ↑CDR2 | 64 | 0.125 | 64 | 8 | 32 | 64 |

[a]MIC values were determined at 24 h both visually and spectrophotometrically.
[b]Fluconazole,
[c]Voriconazole;
numbers in parentheses represent the number of mutation on the gene.

All compounds 16-19 proved to be active against *C. albicans* and *C. glabrata* fluconazole resistant strains. Compound 17 resulted more active than voriconazole itself against mutant strains DSY289, DSY296 and DSY775. Compound 18 was more active than fluconazole but in general less active than compounds 16 and 17 and voriconazole, except for DSY289 strain.

Chitinase Inhibition Assays

Chitinase inhibition assays were conducted against an example of the GH18 family of chitinases, i.e the chitinase enzyme extracted from *Trichoderma viride*. This enzyme has an high degree of identity compared to chitinase 4 of *Candida albicans*, and is commercially available from Sigma-Aldrich (catalogue ID: C8241). The chitinolytic enzymes from *T. viride* are a mixture of extracellular chitinolytic enzymes, which exhibit exo- and endochitinase activities. The major activity was found to be that of N-acetyl-β-glucosaminidase.

The substrate used was the NP-GlcNAc (Sigma-Aldrich, catalogue ID: N9376) dissolved in MES 50 mM at pH6.0; the final concentration was 250 µM. The enzyme was resuspended at 0.11 mg/ml in MES 50 mM at pH 6.0, with a final concentration for the assay of 73 nM diluting with MES 50 mM and BSA 20 µg/ml at pH 6.0. A stock solution of the inhibitors was prepared at 50 mM in DMSO 100%.

The mixture with the inhibitor at various concentrations and the enzyme was prepared directly into the reading plate and left to incubate at room temperature for 20 minutes or three hours. At the end of the incubation times, the substrate was added and the reading was conducted by recording the values up to a maximum time of 10 minutes. The substrate concentration was measured by reading UV absorption at 300 nm ($\varepsilon_M^{300}$: 11100), while, the product of hydrolysis were measured at 400 nm ($\Delta\varepsilon_M^{400}$: 2120). Both IC$_{50}$ and K$_i$ can be calculated.

The results for compound 17, one of the most active compound against *candida* strains, are reported in Table 4. For comparison, the inventors have also tested compounds disclosed in WO2009/113033 (reference compounds 34-39).

Compound 34: 1-(cyclopropylmethyl)-3-[8-(4-imino-2-oxo-1,3,5-triazacyclotridec-1-yl)octyl]guanidine

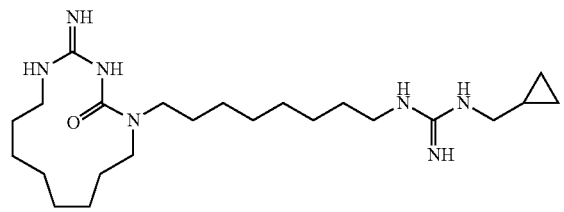

Compound 35: 1-[(E)-but-2-enyl]-3-[8-(4-imino-2-oxo-1,3,5-triazacyclotridec-1-yl)octyl]guanidine

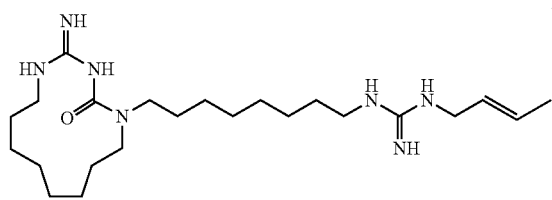

Compound 36: 1-[(E)-but-2-enyl]-3-[6-(4-imino-2-oxo-1,3,5-triazacyclotridec-1-yl)hexyl]guanidine

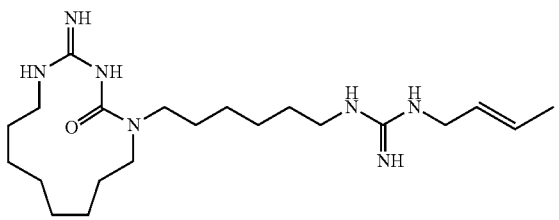

Compound 37: 1-[6-(4-imino-2-oxo-1,3,5-triazacyclotridec-1-yl)hexyl]-3-(2-methylprop-2-enyl)guanidine

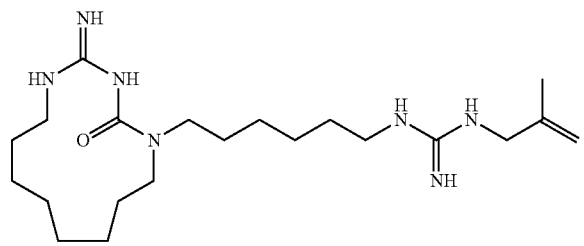

Compound 38: 1-ethyl-3-[6-(4-imino-2-oxo-1,3,5-triazacyclotridec-1-yl)hexyl]guanidine

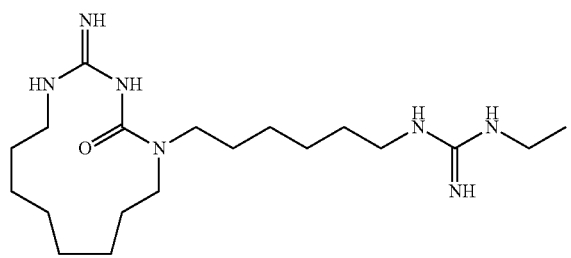

Compound 39: 1-[6-(4-imino-2-oxo-1,3,5-triazacyclotridec-1-yl)hexyl]-3-prop-2-ynylguanidine

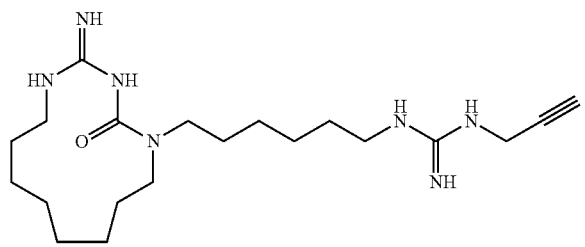

TABLE 4

Inhibition assay of chitinase from *Thricoderma viride* of compound 17 and prior art compounds 34-39.

| Inhibitor | Enz.-inhib. incubation time 20 min | | | Enz.-inhib. incubation time 3 h | | |
|---|---|---|---|---|---|---|
| | Inhib. con. range [µM] | $IC_{50}$ [µM] | $K_i$ [µM] | Inhib. con. range [µM] | $IC_{50}$ [µM] | $K_i$ [µM] |
| 17 | 640-20 | 151 | 48.8 | 1000-10 | 55 | 17.8 |
| 34 | 640-20 | 252 | 81.4 | 1000-10 | 130 | 42 |

TABLE 4-continued

Inhibition assay of chitinase from *Thricoderma viride* of compound 17 and prior art compounds 34-39.

| Inhibitor | Enz.-inhib. incubation time 20 min | | | Enz.-inhib. incubation time 3 h | | |
|---|---|---|---|---|---|---|
| | Inhib. con. range [µM] | $IC_{50}$ [µM] | $K_i$ [µM] | Inhib. con. range [µM] | $IC_{50}$ [µM] | $K_i$ [µM] |
| 35 | 640-40 | 185 | 59.6 | 1000-40 | 157 | 50.8 |
| 36 | — | — | — | 1000-10 | 111 | 35.8 |
| 37 | 640-40 | 276 | 81.4 | 1000-10 | 108 | 34.8 |
| 38 | 640-80 | 508 | 163.9 | 1000-10 | 140 | 45.3 |
| 39 | 640-40 | 170 | 55 | 1000-10 | 97 | 31.3 |

Compound 17 (with the aromatic ring fused in the macrocyclic core) is an active inhibitor of the chitinase enzyme. This compound is more active than compounds 34-39. It is worth to note that the $IC_{50}$ values decrease with time, suggesting a slow binding of the inhibitor.

REFERENCES

1. Groll, A. H.; Lumb, J., New developments in invasive fungal disease. *Future Microbiol.* 2012, 7 (2), 179-84.
2. Mishra, N. N.; Prasad, T.; Sharma, N.; Payasi, A.; Prasad, R.; Gupta, D. K.; Singh, R., Pathogenicity and drug resistance in *Candida albicans* and other yeast species. A review. *Acta Microbiol. Immunol. Hung.* 2007, 54 (3), 201-35.
3. Casalinuovo, I. A.; Di Francesco, P.; Garaci, E., Fluconazole resistance in *Candida albicans*: a review of mechanisms. *Eur. Rev. Med. Pharmacol. Sci.* 2004, 8 (2), 69-77.
4. Manetti, F.; Castagnolo, D.; Raffi, F.; Zizzari, A. T.; Rajamaki, S.; D'Arezzo, S.; Visca, P.; Cona, A.; Fracasso, M. E.; Doria, D.; Posteraro, B.; Sanguinetti, M.; Fadda, G.; Botta, M., Synthesis of new linear guanidines and macrocyclic amidinourea derivatives endowed with high antifungal activity against *Candida* spp. and *Aspergillus* spp. *J. Med. Chem.* 2009, 52 (23), 7376-9.
5. Botta, M.; Raffi, F.; Visca, P. Linear and cyclic guanidine derivatives as antifungal agents and their method of preparation. WO2009113033A2, 2009.
6. Kuranda, M. J.; Robbins, P. W., Chitinase is required for cell separation during growth of *Saccharomyces cerevisiae*. *J. Biol. Chem.* 1991, 266 (29), 19758-67.
7. Sakuda, S., Studies on the chitinase inhibitors, allosamidins. In Chitin enzymology, Muzzarelli, R. A. A., Ed. Atec Edizioni: 1996; Vol. 2, pp 203-212.
8. Takaya, N.; Yamazaki, D.; Horiuchi, H.; Ohta, A.; Takagi, M., Cloning and characterization of a chitinase-encoding gene (chiA) from *Aspergillus nidulans*, disruption of which decreases germination frequency and hyphal growth. *Biosci. Biotechnol. Biochem.* 1998, 62 (1), 60-5.
9. Zhu, Z.; Zheng, T.; Homer, R. J.; Kim, Y.-K.; Chen, N. Y.; Cohn, L.; Hamid, Q.; Elias, J. A., Acidic Mammalian Chitinase in Asthmatic Th2 Inflammation and IL-13 Pathway Activation. *Science* 2004, 304 (5677), 1678-1682.
10. Boot et al., Identification of a novel acidic mammalian chitinase distinct from chitotriosidase. *J. Biol. Chem.* 2001, 276, 6770-8.
11. Hartl. D.; et al., Acidic Mammalian Chitinase Regulates Epithelial Cell Apoptosis via a Chitinolytic-Independent Mechanism. *J-Immunolol* 2009; 182:5098-5106.

The invention claimed is:

1. A compound having the general formula 8:

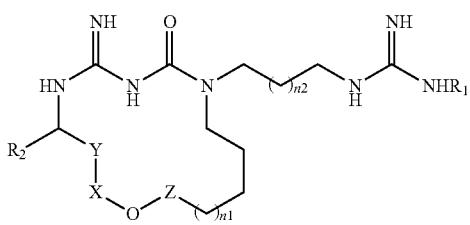

wherein $n_1$ is a number from 0 to 4;

$n_2$ is a number from 1 to 7;

$R_1$ is H; linear or branched $C_1$-$C_6$ alkyl; propargyl, cyclopropylmethyl, but-2-en-1-yl, γ-methylallyl, β-methylallyl, γ,γ-dimethylallyl, benzyl, allyl, pyridin-ylmethyl; methylcarbamoyl, ethylcarbamoyl, propylcarbamoyl, or prop-2-enylcarbamoyl;

$R_2$ is H or

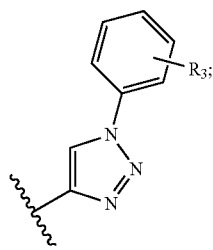

$R_3$ is OH, nitro, $NH_2$, $NHR_8$, $NR_9R_{10}$, $C_1$-$C_6$ alkyl, COOH, $CONH_2$, $CONR_{11}H$, $CONR_{12}R_{13}$, cyano, F, Cl, or Br;

wherein $R_8$, $R_9$, $R_{10}$, $R_{11}$, $R_{12}$, and $R_{13}$, are the same or each independently $C_1$-$C_6$ alkyl, methylcyclopropyl or propan-2-yl;

X is $CH_2$ or C(=O);

Y is $CH_2$, or

X—Y is

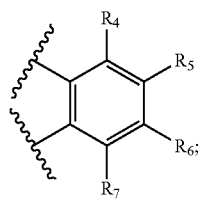

wherein $R_4$, $R_5$, $R_6$, and $R_7$ are the same or each independently H, OH, nitro, $NH_2$, $NHR_{14}$, $NR_{15}R_{16}$, $C_1$-$C_6$ alkyl, COOH, $CONH_2$, $CONR_{17}H$, $CONR_{18}R_{19}$, cyano, F, Cl, or Br; and wherein $R_{14}$, $R_{15}$, $R_{16}$, $R_{17}$, $R_{18}$, and $R_{19}$ are the same or each independently $C_1$-$C_6$ alkyl, methylcyclopropyl or propan-2-yl; and Z is $CH_2$,

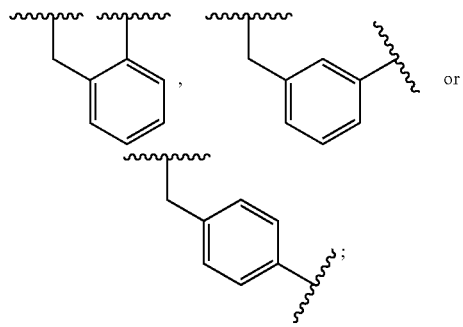

or pharmaceutically acceptable salts thereof.

2. The compound according to claim 1 wherein $R_2$ is

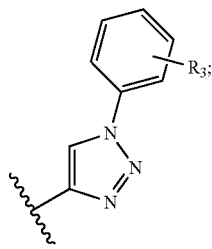

X—Y is

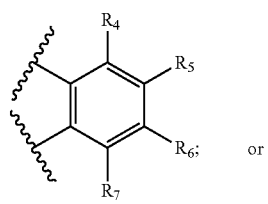

Z is $CH_2$;

or pharmaceutically acceptable salts thereof.

3. The compound according to claim 1 wherein $R_2$ is H;

X—Y is

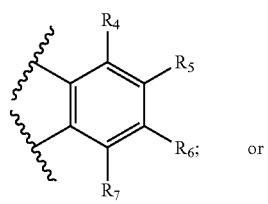

Z is

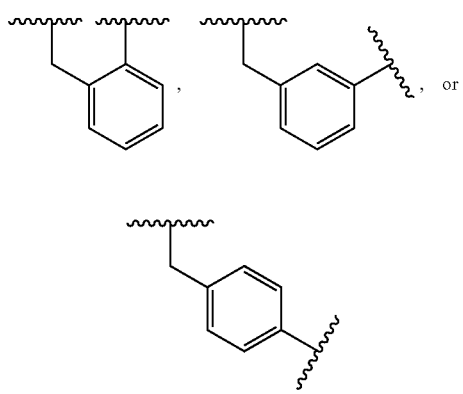 [SMILES: *Cc1ccccc1* ; *Cc1cccc(*)c1 ; *Cc1ccc(*)cc1]

or pharmaceutically acceptable salts thereof.

4. The compound according to claim 1 having formula 8a

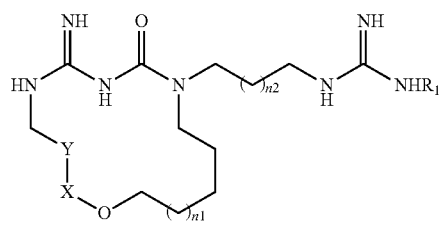
8a or pharmaceutically acceptable salts thereof.

5. The compound according to claim 4 wherein X—Y is

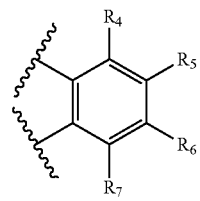

with $R_4$, $R_5$, $R_6$ and $R_7$=H or pharmaceutically acceptable salts thereof.

6. The compound according to claim 4 wherein X is C(=O) and Y is $CH_2$, or pharmaceutically acceptable salts thereof.

7. The compound according to claim 1 selected from:

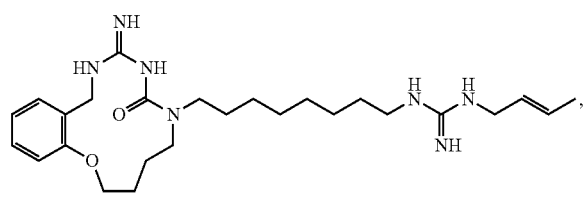
16

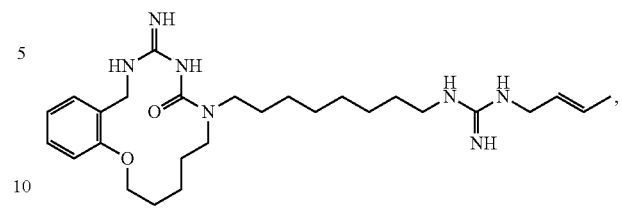
17

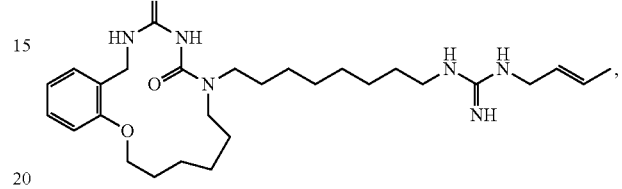
18

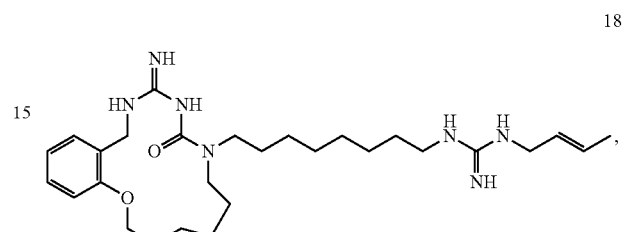
19

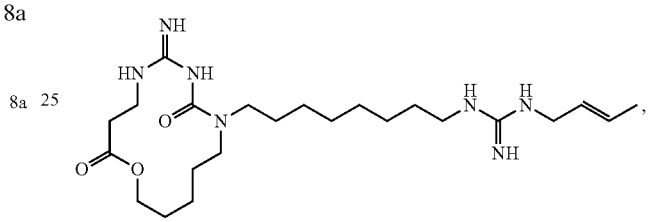
20

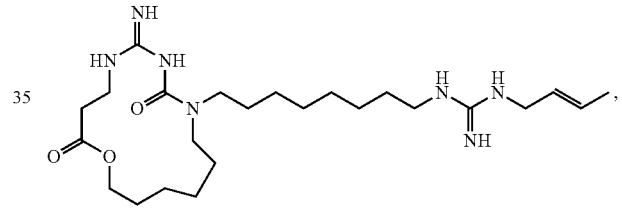
21

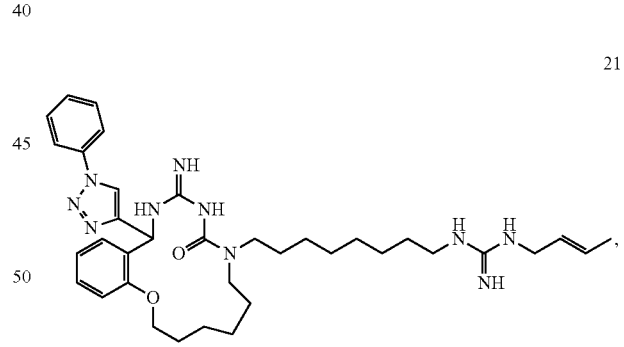
22

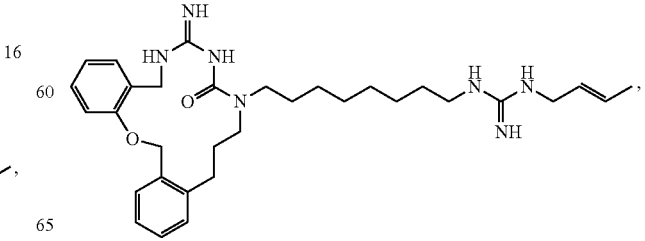

-continued
and

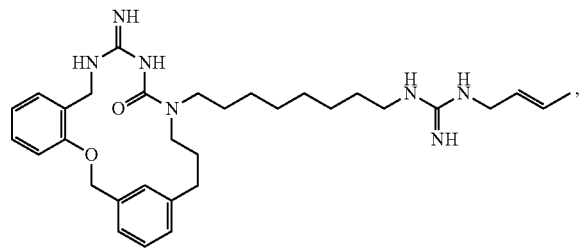

or pharmaceutically acceptable salts thereof.

8. A pharmaceutical composition comprising at least one compound according to claim 1 and appropriate excipients or diluents.

9. The pharmaceutical composition according to claim 8 further comprising at least one therapeutic agent selected from the group consisting of: an antifungal agent, and an anti-inflammatory agent.

10. The pharmaceutical composition according to claim 9 wherein the further antifungal agent is selected from the group consisting of: amphotericin, Amphotericin B, Candicidin, Filipin, Hamycin, Natamycin, Nystatin, Rimocidin, Imidazole, triazole, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole; Albaconazole, Fluconazole, Isavuconazole, Itraconazole, Posaconazole, Ravuconazole, Terconazole, Voriconazole; Abafungi; Amorolfin, Butenafine, Naftifine, Terbinafine; Anidulafungin, Caspofungin, Micafungin; Benzoic acid; Ciclopirox; Flucytosine; Griseofulvin; Haloprogin; Tolnaftate; Undecylenic acid; Crystal violet and Balsam of Peru.

11. A process for the preparation of a compound of formula 8

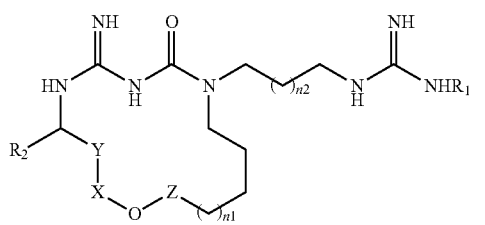

said process comprising the following steps:
i) reacting a compound of formula 2

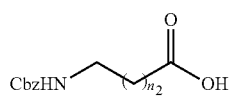

in the presence of AllylNH$_2$, N-(3-Dimethylaminopropyl)-N'-ethylcarbodiimide hydrochloride [EDC], 1-hydroxybenzotriazole [HOBt], and N,N'-Diisopylethylamine [DIPEA] in N,N-dimethylformamide [DMF] to obtain a resultant compound:

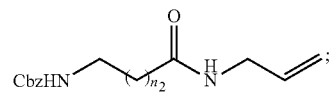

ii) reacting the resultant compound of step (i) with diisobutylaluminium hydride [DIBAL-H] in dichloromethane [DCM] at room temperature to obtain a compound of formula 3

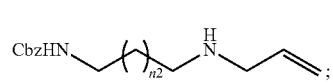

iii) reacting the compound of formula 3 of step (ii) with a compound of formula 1 in tetrahydrofuran [THF] under reflux for 12 h to obtain a compound of formula 4

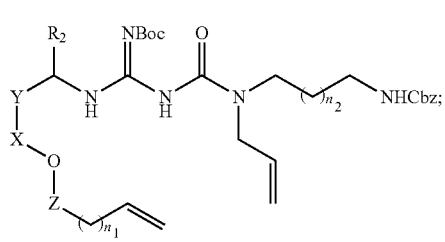

iv) reacting the compound of formula 4 of step (iii) in the presence of a second generation Grubbs' catalyst in toluene or DCM at a concentration of 2-10 mM at 40-80° C. to obtain a compound of formula 5

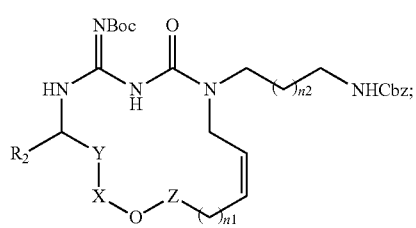

v) reacting the compound of formula 5 of step (iv) with hydrogen over palladium on carbon [Pd/C] in ethanol [EtOH] to obtain a compound of formula 6

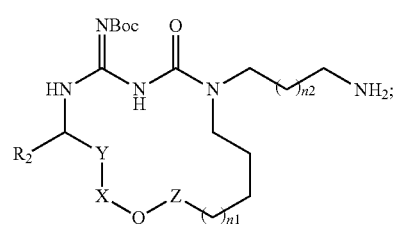

vi) reacting the compound of formula 6 of step (v) with R$_1$NBoc(C=NBoc)SMe in THF under reflux for 12 h to obtain a compound of formula 7

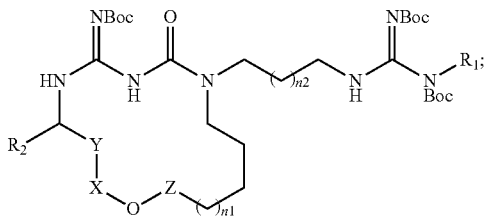

vii) reacting the compound of formula 7 of step (vi) with TFA to obtain a compound of Formula 8, or a pharmaceutically acceptable salts thereof, wherein
n$_1$ is a number from 0 to 4;
n$_2$ s a number from 1 to 7;
R$_1$ is H; linear or branched C$_1$-C$_6$ alkyl; propargyl, cyclopropylmethyl, but-2-en-1-yl, γ-methylallyl, β-methylallyl, γ,γ-dimethylallyl, benzyl, alkyl, pyridin-ylmethyl; methylcarbamoyl, ethylcarbamoyl, propylcarbamoyl, or prop-2-enylcarbamoyl;
R$_2$ is H or

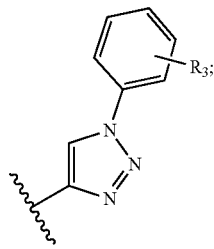

R$_3$ is OH, nitro, NH$_2$, NHR$_8$, NR$_9$R$_{10}$, C$_1$-C$_6$ alkyl, COOH, CONH$_2$, CONR$_{11}$H, CONR$_{12}$R$_{13}$, cyano, F, Cl, or Br;
wherein
R$_8$, R$_9$, R$_{10}$, R$_{11}$, R$_{12}$, a R$_{13}$, are the same or each independently C$_1$-C$_6$ alkyl, methylcyclopropyl or propan-2-yl;
X is CH$_2$ or C(=O);
Y is CH$_2$, or
X—Y is

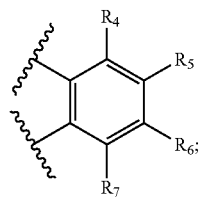

wherein R$_4$, R$_5$, R$_6$, and R$_7$ are the same or each independently H, OH, nitro, NH$_2$, NHR$_{14}$, NR$_{15}$R$_{16}$, C$_1$-C$_6$ alkyl, COOH, CONH$_2$, CONR$_{17}$H, CONR$_{18}$R$_{19}$, cyano, F, Cl, or Br; and wherein R$_{14}$, R$_{15}$, R$_{16}$, R$_{17}$, R$_{18}$, and R$_{19}$ are the same or each independently C$_1$-C$_6$ alkyl, methylcyclopropyl or propan-2-yl;
and
Z is CH$_2$,

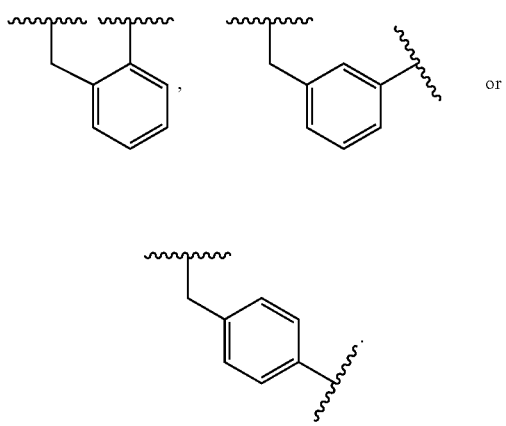

12. A method for inhibiting a chitinase in a mammal comprising administering the compound according to claim 1 in a suitable amount to the mammal in need thereof.

13. A method for treating a fungal infection in a mammal comprising administering the compound according to claim 1 in a suitable amount to the mammal in need thereof.

14. The method according to claim 13, wherein the fungal infection is of a *Candida* species.

15. The method according to claim 14, wherein the *Candida* species is selected from the group consisting of: *C. albicans, C. guilliermondii, C. krusei, C. parapsilosis, C. tropicalis, C. kefyr* and *C. glabrata*.

16. The method according to claim 14 wherein the *Candida* species is drug resistant.

17. The method according to claim 16 wherein the *Candida* species is resistant to fluconazole and/or voriconazole.

18. A method for treating an IL-13 and/or Th-2-mediated disease in a mammal comprising administering the compound according to claim 1 in a suitable amount to the mammal in need thereof.

19. The method according to claim 18 wherein the IL-13 and/or Th-2-mediated disease is asthma.

20. The method according to claim 18 wherein the IL-13 and/or Th-2-mediated disease is a Th-2-mediated inflammation.

21. The method according to claim 18 wherein the IL-13 and/or Th-2-mediated disease is an allergic airway disease.

* * * * *